(12) United States Patent
Marczyk et al.

(10) Patent No.: US 11,510,674 B2
(45) Date of Patent: *Nov. 29, 2022

(54) MULTI-FIRE LEAD SCREW STAPLING DEVICE

(71) Applicant: Covidien LP, Mansfield, MA (US)

(72) Inventors: Stanislaw Marczyk, Stratford, CT (US); Simon R. Grover, Cambridge (GB); Alistair Ward, Swavesey (GB); Gary Stacey, Cambridge (GB)

(73) Assignee: Covidien LP, Mansfield, MA (US)

( * ) Notice: Subject to any disclaimer, the term of this patent is extended or adjusted under 35 U.S.C. 154(b) by 304 days.

This patent is subject to a terminal disclaimer.

(21) Appl. No.: 16/458,613

(22) Filed: Jul. 1, 2019

(65) Prior Publication Data
US 2019/0321042 A1 Oct. 24, 2019

Related U.S. Application Data

(63) Continuation of application No. 15/150,611, filed on May 10, 2016, now Pat. No. 10,349,941.
(Continued)

(51) Int. Cl.
*A61B 17/072* (2006.01)
*A61B 17/10* (2006.01)
(Continued)

(52) U.S. Cl.
CPC .......... *A61B 17/105* (2013.01); *A61B 17/068* (2013.01); *A61B 17/0644* (2013.01);
(Continued)

(58) Field of Classification Search
CPC ............ A61B 17/105; A61B 17/07207; A61B 17/068; A61B 17/0644; A61B 17/072;
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

AU 198654765 9/1986
CA 2773414 A1 11/2012
(Continued)

OTHER PUBLICATIONS

U.S. Appl. No. 15/150,606, filed May 10, 2016, inventor Stanislaw Marczyk.
(Continued)

*Primary Examiner* — Robert F Long

(57) ABSTRACT

A surgical stapling device comprises a housing and a plurality of cartridges that are coupled together to form a barrel that is rotatably supported within the housing. Each of the cartridges defines a plurality of staple pockets that support a plurality of staples. An anvil is pivotally coupled to the housing and is movable in relation to the barrel between an open position and a clamped position. A drive shaft extends through the housing and through the barrel and a pusher operatively connected to the drive shaft. The pusher is configured to translate through the barrel to eject the staples from the plurality of cartridges in response to actuation of the drive shaft. The barrel is positioned within the housing to align a first one of the plurality of cartridges with the anvil to eject the staples from the first cartridge upon movement of the pusher within the barrel through a first firing stroke and subsequently rotatable within the housing to align a second one of the plurality of cartridges with the anvil to eject the staples from the second cartridge upon movement of the pusher within the barrel through a second firing stroke.

10 Claims, 22 Drawing Sheets

Related U.S. Application Data

(60) Provisional application No. 62/166,979, filed on May 27, 2015.

(51) Int. Cl.
*A61B 17/064* (2006.01)
*A61B 17/068* (2006.01)
*A61B 17/00* (2006.01)
*A61B 17/29* (2006.01)
*A61B 90/00* (2016.01)

(52) U.S. Cl.
CPC ...... *A61B 17/072* (2013.01); *A61B 17/07207* (2013.01); *A61B 2017/00398* (2013.01); *A61B 2017/07221* (2013.01); *A61B 2017/07228* (2013.01); *A61B 2017/07271* (2013.01); *A61B 2017/07278* (2013.01); *A61B 2017/07285* (2013.01); *A61B 2017/2903* (2013.01); *A61B 2017/2927* (2013.01); *A61B 2090/034* (2016.02)

(58) Field of Classification Search
CPC .. A61B 2017/2927; A61B 2017/07278; A61B 2017/07221; A61B 2017/07285; A61B 2017/00398; A61B 2017/07228; A61B 2017/07271; A61B 2017/2903; A61B 2090/034; A61B 17/00234; A61B 17/1155; A61B 2017/0046; A61B 2017/00199; A61B 2090/035
USPC ............ 227/181.1–182.1; 606/219–221
See application file for complete search history.

(56) References Cited

U.S. PATENT DOCUMENTS

| | | | |
|---|---|---|---|
| 3,499,591 A | 3/1970 | Green | |
| 3,675,688 A * | 7/1972 | Bryan | A61B 17/128 227/19 |
| 3,735,762 A * | 5/1973 | Bryan | A61B 17/128 606/143 |
| 3,777,538 A | 12/1973 | Weatherly et al. | |
| 3,882,854 A | 5/1975 | Hulka et al. | |
| 4,027,510 A | 6/1977 | Hiltebrandt | |
| 4,086,926 A | 5/1978 | Green et al. | |
| 4,241,861 A | 12/1980 | Fleischer | |
| 4,244,372 A | 1/1981 | Kapitanov et al. | |
| 4,275,813 A * | 6/1981 | Noiles | A61B 17/105 428/913 |
| 4,429,695 A | 2/1984 | Green | |
| 4,487,394 A * | 12/1984 | Rothfuss | A61B 17/076 254/28 |
| 4,505,414 A | 3/1985 | Filipi | |
| 4,520,817 A | 6/1985 | Green | |
| 4,526,174 A * | 7/1985 | Froehlich | A61B 17/0684 206/438 |
| 4,589,413 A | 5/1986 | Malyshev et al. | |
| 4,596,351 A | 6/1986 | Fedotov et al. | |
| 4,602,634 A | 7/1986 | Barkley | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,655,222 A * | 4/1987 | Florez | A61L 31/10 606/219 |
| 4,671,445 A | 6/1987 | Barker et al. | |
| 4,700,703 A | 10/1987 | Resnick et al. | |
| 4,703,887 A | 11/1987 | Clanton et al. | |
| 4,706,864 A * | 11/1987 | Jacobsen | B25C 1/001 227/109 |
| 4,719,917 A * | 1/1988 | Barrows | A61L 31/06 606/220 |
| 4,728,020 A | 3/1988 | Green et al. | |
| 4,749,114 A * | 6/1988 | Green | A61B 17/11 227/19 |
| 4,752,024 A | 6/1988 | Green et al. | |
| 4,773,420 A * | 9/1988 | Green | A61B 17/11 227/178.1 |
| 4,784,137 A | 11/1988 | Kulik et al. | |
| 4,787,387 A * | 11/1988 | Burbank, III | A61B 17/0644 227/176.1 |
| 4,802,478 A * | 2/1989 | Powell | A61B 17/0684 606/138 |
| 4,863,088 A | 9/1989 | Redmond et al. | |
| 4,869,415 A | 9/1989 | Fox | |
| 4,887,601 A * | 12/1989 | Richards | A61B 17/0644 606/219 |
| 4,892,244 A | 1/1990 | Fox et al. | |
| 4,930,674 A * | 6/1990 | Barak | A61B 17/072 227/179.1 |
| 4,955,959 A | 9/1990 | Tompkins et al. | |
| 4,978,049 A | 12/1990 | Green | |
| 4,991,764 A | 2/1991 | Mericle | |
| 5,014,899 A | 5/1991 | Presty et al. | |
| 5,031,814 A | 7/1991 | Tompkins et al. | |
| 5,040,715 A | 8/1991 | Green et al. | |
| 5,065,929 A | 11/1991 | Schulze et al. | |
| 5,069,097 A * | 12/1991 | Mori | B26D 1/185 83/458 |
| 5,071,430 A | 12/1991 | de Salis et al. | |
| 5,074,454 A | 12/1991 | Peters | |
| 5,083,695 A | 1/1992 | Foslien et al. | |
| 5,084,057 A | 1/1992 | Green et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,156,315 A | 10/1992 | Green et al. | |
| 5,156,614 A | 10/1992 | Green et al. | |
| 5,163,943 A | 11/1992 | Mohiuddin et al. | |
| 5,170,925 A | 12/1992 | Madden et al. | |
| 5,171,247 A | 12/1992 | Hughett et al. | |
| 5,173,133 A | 12/1992 | Morin et al. | |
| 5,180,092 A | 1/1993 | Crainich | |
| 5,188,274 A | 2/1993 | Moeinzadeh et al. | |
| 5,192,288 A * | 3/1993 | Thompson | A61B 17/128 227/901 |
| 5,220,928 A | 6/1993 | Oddsen et al. | |
| 5,221,036 A | 6/1993 | Takase | |
| 5,242,457 A | 9/1993 | Akopov et al. | |
| 5,246,156 A | 9/1993 | Rothfuss et al. | |
| 5,253,793 A | 10/1993 | Green et al. | |
| 5,263,629 A | 11/1993 | Trumbull et al. | |
| RE34,519 E | 1/1994 | Fox et al. | |
| 5,275,323 A | 1/1994 | Schulze et al. | |
| 5,282,807 A | 2/1994 | Knoepfler | |
| 5,282,829 A * | 2/1994 | Hermes | A61B 17/064 411/479 |
| 5,289,963 A | 3/1994 | McGarry et al. | |
| 5,307,976 A | 5/1994 | Olson et al. | |
| 5,308,576 A | 5/1994 | Green et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,330,486 A | 7/1994 | Wilk | |
| 5,332,142 A | 7/1994 | Robinson et al. | |
| 5,336,232 A | 8/1994 | Green et al. | |
| 5,344,061 A | 9/1994 | Crainich | |
| 5,352,238 A | 10/1994 | Green et al. | |
| 5,356,064 A | 10/1994 | Green et al. | |
| 5,358,506 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,366,133 A | 11/1994 | Geiste | |
| 5,376,095 A | 12/1994 | Ortiz | |
| 5,379,933 A | 1/1995 | Green et al. | |
| 5,381,943 A | 1/1995 | Allen et al. | |
| 5,382,255 A | 1/1995 | Castro et al. | |

(56) References Cited

U.S. PATENT DOCUMENTS

| | | | |
|---|---|---|---|
| 5,383,880 A | 1/1995 | Hooven | |
| 5,389,098 A * | 2/1995 | Tsuruta | A61B 17/00234 606/41 |
| 5,395,030 A * | 3/1995 | Kuramoto | A61B 1/00087 227/179.1 |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,403,312 A | 4/1995 | Yates et al. | |
| 5,403,326 A * | 4/1995 | Harrison | A61B 17/10 227/181.1 |
| 5,405,072 A | 4/1995 | Zlock et al. | |
| 5,407,293 A | 4/1995 | Crainich | |
| 5,413,268 A | 5/1995 | Green et al. | |
| 5,415,334 A | 5/1995 | Williamson et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,423,857 A * | 6/1995 | Rosenman | A61B 17/064 411/457 |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,441,193 A | 8/1995 | Gravener | |
| 5,445,304 A | 8/1995 | Plyley et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A * | 2/1996 | Plyley | A61B 17/064 227/176.1 |
| 5,490,856 A | 2/1996 | Person et al. | |
| 5,497,933 A * | 3/1996 | DeFonzo | A61B 17/0684 227/175.1 |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,549,628 A | 8/1996 | Cooper et al. | |
| 5,551,622 A * | 9/1996 | Yoon | A61B 17/072 227/176.1 |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A | 10/1996 | Huitema et al. | |
| 5,564,615 A | 10/1996 | Bishop et al. | |
| 5,571,116 A | 11/1996 | Bolanos et al. | |
| 5,573,169 A | 11/1996 | Green et al. | |
| 5,573,543 A * | 11/1996 | Akopov | A61B 17/04 227/175.1 |
| 5,575,799 A | 11/1996 | Bolanos et al. | |
| 5,575,803 A | 11/1996 | Cooper et al. | |
| 5,577,654 A | 11/1996 | Bishop | |
| 5,582,616 A * | 12/1996 | Bolduc | A61B 17/064 606/139 |
| 5,584,425 A | 12/1996 | Savage et al. | |
| 5,586,711 A * | 12/1996 | Plyley | A61B 17/064 227/176.1 |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,643,291 A * | 7/1997 | Pier | A61B 17/1285 606/143 |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,665,085 A | 9/1997 | Nardella | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,690,269 A | 11/1997 | Bolanos et al. | |
| 5,690,675 A | 11/1997 | Sawyer et al. | |
| 5,692,668 A | 12/1997 | Schulze et al. | |
| 5,697,542 A | 12/1997 | Knodel et al. | |
| 5,702,409 A | 12/1997 | Rayburn et al. | |
| 5,704,534 A | 1/1998 | Huitema et al. | |
| 5,706,997 A | 1/1998 | Green et al. | |
| 5,709,334 A | 1/1998 | Sorrentino et al. | |
| 5,711,472 A | 1/1998 | Bryan | |
| 5,713,505 A | 2/1998 | Huitema | |
| 5,715,988 A | 2/1998 | Palmer | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,728,110 A | 3/1998 | Vidal et al. | |
| 5,732,806 A | 3/1998 | Foshee et al. | |
| 5,735,848 A | 4/1998 | Yates et al. | |
| 5,743,456 A | 4/1998 | Jones et al. | |
| 5,749,893 A | 5/1998 | Vidal et al. | |
| 5,752,644 A | 5/1998 | Bolanos et al. | |

(56) References Cited

U.S. PATENT DOCUMENTS

| | | | |
|---|---|---|---|
| 5,762,255 | A | 6/1998 | Chrisman et al. |
| 5,762,256 | A | 6/1998 | Mastri et al. |
| 5,769,303 | A | 6/1998 | Knodel et al. |
| 5,769,892 | A | 6/1998 | Kingwell |
| 5,772,099 | A | 6/1998 | Gravener |
| 5,772,673 | A | 6/1998 | Cuny et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,834 | A | 7/1998 | Lucey et al. |
| 5,785,232 | A | 7/1998 | Vidal et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,811 | A | 9/1998 | Yates et al. |
| 5,810,855 | A | 9/1998 | Rayburn et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,109 | A | 10/1998 | McGarry et al. |
| 5,820,009 | A | 10/1998 | Melling et al. |
| 5,823,066 | A | 10/1998 | Huitema et al. |
| 5,826,776 | A | 10/1998 | Schulze et al. |
| 5,829,662 | A | 11/1998 | Allen et al. |
| 5,833,695 | A | 11/1998 | Yoon |
| 5,836,147 | A | 11/1998 | Schnipke |
| 5,862,972 | A | 1/1999 | Green et al. |
| 5,865,361 | A | 2/1999 | Milliman et al. |
| 5,871,135 | A | 2/1999 | Williamson, IV et al. |
| 5,873,873 | A | 2/1999 | Smith et al. |
| 5,878,938 | A | 3/1999 | Bittner et al. |
| 5,893,506 | A | 4/1999 | Powell |
| 5,893,855 | A * | 4/1999 | Jacobs ............... A61B 17/0684 606/150 |
| 5,894,979 | A | 4/1999 | Powell |
| 5,897,562 | A | 4/1999 | Bolanos et al. |
| 5,901,895 | A | 5/1999 | Heaton et al. |
| 5,911,352 | A | 6/1999 | Racenet et al. |
| 5,911,353 | A | 6/1999 | Bolanos et al. |
| 5,918,791 | A | 7/1999 | Sorrentino et al. |
| 5,919,198 | A | 7/1999 | Graves, Jr. et al. |
| 5,922,001 | A | 7/1999 | Yoon |
| 5,931,847 | A | 8/1999 | Bittner et al. |
| 5,941,442 | A | 8/1999 | Geiste et al. |
| 5,954,259 | A | 9/1999 | Viola et al. |
| 5,957,430 | A * | 9/1999 | Olson ..................... B25C 11/02 254/28 |
| 5,964,774 | A | 10/1999 | McKean et al. |
| 5,980,510 | A | 11/1999 | Tsonton et al. |
| 5,988,479 | A | 11/1999 | Palmer |
| 6,004,335 | A | 12/1999 | Vaitekunas et al. |
| 6,010,054 | A | 1/2000 | Johnson et al. |
| 6,032,849 | A | 3/2000 | Mastri et al. |
| 6,045,560 | A | 4/2000 | McKean et al. |
| 6,059,787 | A * | 5/2000 | Allen ................. A61B 17/0642 606/75 |
| 6,063,097 | A | 5/2000 | Oi et al. |
| 6,079,606 | A | 6/2000 | Milliman et al. |
| 6,099,551 | A | 8/2000 | Gabbay |
| 6,109,500 | A | 8/2000 | Alli et al. |
| 6,131,789 | A | 10/2000 | Schulze et al. |
| 6,131,790 | A | 10/2000 | Piraka |
| 6,155,473 | A | 12/2000 | Tompkins et al. |
| 6,165,204 | A * | 12/2000 | Levinson ........... A61B 17/0487 606/232 |
| 6,197,017 | B1 | 3/2001 | Brock et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,254,615 | B1 * | 7/2001 | Bolduc ............ A61B 17/12136 606/151 |
| 6,264,086 | B1 | 7/2001 | McGuckin, Jr. |
| 6,264,087 | B1 | 7/2001 | Whitman |
| 6,279,809 | B1 | 8/2001 | Nicolo |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,391,038 | B2 | 5/2002 | Vargas et al. |
| 6,398,797 | B2 | 6/2002 | Bombard et al. |
| 6,419,682 | B1 * | 7/2002 | Appleby ............ A61B 17/1222 206/339 |
| 6,436,097 | B1 | 8/2002 | Nardella |
| 6,439,446 | B1 | 8/2002 | Perry et al. |
| 6,443,973 | B1 | 9/2002 | Whitman |
| 6,478,804 | B2 | 11/2002 | Vargas et al. |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,602,252 | B2 | 8/2003 | Mollenauer |
| 6,619,529 | B2 | 9/2003 | Green et al. |
| D480,808 | S | 10/2003 | Wells et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,681,978 | B2 | 1/2004 | Geiste et al. |
| 6,698,643 | B2 | 3/2004 | Whitman |
| 6,716,232 | B1 | 4/2004 | Vidal et al. |
| 6,722,552 | B2 | 4/2004 | Fenton, Jr. |
| 6,755,338 | B2 | 6/2004 | Hahnen et al. |
| 6,783,524 | B2 | 8/2004 | Anderson et al. |
| 6,786,382 | B1 | 9/2004 | Hoffman |
| 6,817,509 | B2 | 11/2004 | Geiste et al. |
| 6,830,174 | B2 | 12/2004 | Hillstead et al. |
| 6,835,199 | B2 | 12/2004 | McGuckin, Jr. et al. |
| 6,843,403 | B2 | 1/2005 | Whitman |
| RE38,708 | E | 3/2005 | Bolanos et al. |
| 6,877,647 | B2 | 4/2005 | Green et al. |
| 6,889,116 | B2 | 5/2005 | Jinno |
| 6,905,057 | B2 | 6/2005 | Swayze et al. |
| 6,945,444 | B2 | 9/2005 | Gresham et al. |
| 6,953,138 | B1 | 10/2005 | Dworak et al. |
| 6,953,139 | B2 | 10/2005 | Milliman et al. |
| 6,959,852 | B2 | 11/2005 | Shelton, IV et al. |
| 6,962,594 | B1 | 11/2005 | Thevenet |
| 6,964,363 | B2 | 11/2005 | Wales et al. |
| 6,978,921 | B2 | 12/2005 | Shelton, IV et al. |
| 6,981,628 | B2 | 1/2006 | Wales |
| 6,981,983 | B1 * | 1/2006 | Rosenblatt ......... A61B 17/0401 128/898 |
| 6,986,451 | B1 | 1/2006 | Mastri et al. |
| 6,988,649 | B2 | 1/2006 | Shelton, IV et al. |
| 6,991,627 | B2 | 1/2006 | Madhani et al. |
| 6,994,714 | B2 | 2/2006 | Vargas et al. |
| 7,000,818 | B2 | 2/2006 | Shelton, IV et al. |
| 7,000,819 | B2 | 2/2006 | Swayze et al. |
| 7,032,799 | B2 | 4/2006 | Viola et al. |
| 7,044,352 | B2 | 5/2006 | Shelton, IV et al. |
| 7,044,353 | B2 | 5/2006 | Mastri et al. |
| 7,055,730 | B2 | 6/2006 | Ehrenfels et al. |
| 7,055,731 | B2 | 6/2006 | Shelton, IV et al. |
| 7,059,508 | B2 | 6/2006 | Shelton, IV et al. |
| 7,070,083 | B2 | 7/2006 | Jankowski |
| 7,083,075 | B2 | 8/2006 | Swayze et al. |
| 7,097,089 | B2 | 8/2006 | Marczyk |
| 7,111,769 | B2 | 9/2006 | Wales et al. |
| 7,114,642 | B2 | 10/2006 | Whitman |
| 7,121,446 | B2 | 10/2006 | Arad et al. |
| 7,128,253 | B2 | 10/2006 | Mastri et al. |
| 7,128,254 | B2 | 10/2006 | Shelton, IV et al. |
| 7,140,527 | B2 | 11/2006 | Ehrenfels et al. |
| 7,140,528 | B2 | 11/2006 | Shelton, IV |
| 7,143,923 | B2 | 12/2006 | Shelton, IV et al. |
| 7,143,924 | B2 | 12/2006 | Scirica et al. |
| 7,143,925 | B2 | 12/2006 | Shelton, IV et al. |

(56) References Cited

U.S. PATENT DOCUMENTS

| | | |
|---|---|---|
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 * | 7/2008 | Racenet ............ A61B 17/0644 227/176.1 |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,699,860 B2 * | 4/2010 | Huitema ............ A61B 17/083 606/158 |

(56) References Cited

U.S. PATENT DOCUMENTS

| | | |
|---|---|---|
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 * | 9/2010 | Hess ............... A61B 17/105 606/219 |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,873 B2 * | 4/2011 | Cummins .......... A61B 17/0644 606/219 |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 * | 4/2011 | Viola ................ A61B 17/105 227/175.1 |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,946,981 B1 * | 5/2011 | Cubb ................ A61B 1/00103 600/187 |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |

(56) References Cited

U.S. PATENT DOCUMENTS

| | | | |
|---|---|---|---|
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,789 | B1 * | 11/2011 | White .................. A61B 17/068 227/176.1 |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, Iv et al. |
| 8,167,186 | B2 | 5/2012 | Racenet et al. |
| 8,172,121 | B2 | 5/2012 | Krehel |
| 8,172,124 | B2 | 5/2012 | Shelton, Iv et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 | 7/2012 | Farascioni et al. |
| 8,225,980 | B1 * | 7/2012 | Rivera ............ A61B 17/07292 227/176.1 |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,240,538 | B1 * | 8/2012 | Manoux ........... A61B 17/07207 227/178.1 |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,261,958 | B1 * | 9/2012 | Knodel ............ A61B 17/07207 227/176.1 |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |
| 8,276,594 | B2 | 10/2012 | Shah |
| 8,276,801 | B2 | 10/2012 | Zemlok et al. |
| 8,276,802 | B2 | 10/2012 | Kostrzewski |
| 8,281,973 | B2 | 10/2012 | Wenchell et al. |
| 8,286,847 | B2 | 10/2012 | Taylor |
| 8,286,848 | B2 | 10/2012 | Wenchell et al. |
| 8,286,850 | B2 | 10/2012 | Viola |
| 8,292,146 | B2 | 10/2012 | Holsten et al. |
| 8,292,147 | B2 | 10/2012 | Viola |
| 8,292,148 | B2 | 10/2012 | Viola |
| 8,292,149 | B2 | 10/2012 | Ivanko |
| 8,292,150 | B2 | 10/2012 | Bryant |
| 8,292,151 | B2 | 10/2012 | Viola |
| 8,292,152 | B2 | 10/2012 | Milliman et al. |
| 8,292,153 | B2 | 10/2012 | Jankowski |
| 8,292,154 | B2 | 10/2012 | Marczyk |
| 8,292,155 | B2 | 10/2012 | Shelton, IV et al. |
| 8,292,156 | B2 | 10/2012 | Kostrzewski |
| 8,292,158 | B2 | 10/2012 | Sapienza |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,044 | B2 | 11/2012 | Viola |
| 8,308,046 | B2 | 11/2012 | Prommersberger |
| 8,308,757 | B2 | 11/2012 | Hillstead et al. |
| 8,317,070 | B2 | 11/2012 | Hueil et al. |
| 8,317,071 | B1 | 11/2012 | Knodel |
| 8,317,072 | B1 | 11/2012 | Knodel et al. |
| 8,322,455 | B2 | 12/2012 | Shelton, IV et al. |
| 8,322,589 | B2 | 12/2012 | Boudreaux |
| 8,328,061 | B2 | 12/2012 | Kasvikis |
| 8,328,065 | B2 | 12/2012 | Shah |
| 8,333,313 | B2 | 12/2012 | Boudreaux et al. |
| 8,336,751 | B2 | 12/2012 | Scirica |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,353,437 | B2 | 1/2013 | Boudreaux |

(56) References Cited

U.S. PATENT DOCUMENTS

| | | | |
|---|---|---|---|
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czemik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,514 B2 * | 12/2013 | Miller .............. A61B 17/0642 227/175.1 |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,631,992 B1 * | 1/2014 | Hausen ............. A61B 17/0644 227/181.1 |
| 8,631,993 B2 | 1/2014 | Kostrzewski |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,369 B1 | 3/2014 | Manoux et al. |
| 8,662,371 B2 | 3/2014 | Viola |
| 8,668,129 B2 | 3/2014 | Olson |
| 8,672,206 B2 | 3/2014 | Aranyi et al. |

(56) References Cited

U.S. PATENT DOCUMENTS

| | | | |
|---|---|---|---|
| 8,672,208 B2 | 3/2014 | Hess et al. | |
| 8,672,209 B2 | 3/2014 | Crainich | |
| 8,678,263 B2 | 3/2014 | Viola | |
| 8,678,990 B2 | 3/2014 | Wazer et al. | |
| 8,679,155 B2 | 3/2014 | Knodel et al. | |
| 8,684,247 B2 | 4/2014 | Scirica et al. | |
| 8,684,249 B2 | 4/2014 | Racenet et al. | |
| 8,690,039 B2 | 4/2014 | Beardsley et al. | |
| 8,695,865 B2 | 4/2014 | Smith et al. | |
| 8,695,866 B2 | 4/2014 | Leimbach et al. | |
| 8,701,958 B2 | 4/2014 | Shelton, IV et al. | |
| 8,701,959 B2 | 4/2014 | Shah | |
| 8,701,961 B2 | 4/2014 | Ivanko | |
| 8,708,213 B2 | 4/2014 | Shelton, IV et al. | |
| 8,714,429 B2 | 5/2014 | Demmy | |
| 8,715,277 B2 | 5/2014 | Weizman | |
| 8,720,766 B2 | 5/2014 | Hess et al. | |
| 8,721,630 B2 | 5/2014 | Ortiz et al. | |
| 8,727,197 B2 | 5/2014 | Hess et al. | |
| 8,727,200 B2 | 5/2014 | Roy | |
| 8,733,612 B2 | 5/2014 | Ma | |
| 8,740,034 B2 | 6/2014 | Morgan et al. | |
| 8,740,039 B2 | 6/2014 | Farascioni | |
| 8,757,465 B2 | 6/2014 | Woodard, Jr. et al. | |
| 8,758,391 B2 | 6/2014 | Swayze et al. | |
| 8,763,877 B2 | 7/2014 | Schall et al. | |
| 8,763,879 B2 | 7/2014 | Shelton, IV et al. | |
| 8,770,458 B2 | 7/2014 | Scirica | |
| 8,777,082 B2 | 7/2014 | Scirica | |
| 8,783,541 B2 | 7/2014 | Shelton, IV et al. | |
| 8,783,542 B2 | 7/2014 | Riestenberg et al. | |
| 8,789,737 B2 | 7/2014 | Hodgkinson et al. | |
| 8,789,738 B2 | 7/2014 | Knodel et al. | |
| 8,789,739 B2 | 7/2014 | Swensgard | |
| 8,800,838 B2 | 8/2014 | Shelton, IV | |
| 8,800,840 B2 | 8/2014 | Jankowski | |
| 8,800,841 B2 | 8/2014 | Ellerhorst et al. | |
| 8,808,311 B2 | 8/2014 | Heinrich et al. | |
| 8,814,024 B2 | 8/2014 | Woodard, Jr. et al. | |
| 8,814,025 B2 | 8/2014 | Miller et al. | |
| 8,820,603 B2 | 9/2014 | Shelton, Iv et al. | |
| 8,820,605 B2 | 9/2014 | Shelton, Iv | |
| 8,820,607 B2 | 9/2014 | Marczyk | |
| 8,827,133 B2 | 9/2014 | Shelton, IV et al. | |
| 8,827,134 B2 | 9/2014 | Viola et al. | |
| 8,833,632 B2 | 9/2014 | Swensgard | |
| 8,840,003 B2 | 9/2014 | Morgan et al. | |
| 8,840,603 B2 | 9/2014 | Shelton, Iv et al. | |
| 8,851,355 B2 | 10/2014 | Aranyi et al. | |
| 8,905,286 B2 | 12/2014 | Kostrzewski | |
| 9,016,546 B2 | 4/2015 | Demmy et al. | |
| 9,027,817 B2 | 5/2015 | Milliman et al. | |
| 9,289,207 B2 | 3/2016 | Shelton, IV | |
| 9,597,076 B2 | 3/2017 | Kostrzewski | |
| 9,655,613 B2* | 5/2017 | Schaller | A61B 17/07207 |
| 9,724,096 B2* | 8/2017 | Thompson | A61B 17/07207 |
| 9,750,502 B2 | 9/2017 | Scirica et al. | |
| 9,775,623 B2 | 10/2017 | Zammataro et al. | |
| 9,788,835 B2* | 10/2017 | Morgan | A61B 17/07207 |
| 9,833,241 B2* | 12/2017 | Huitema | A61B 17/07292 |
| 9,848,874 B2 | 12/2017 | Kostrzewski | |
| 9,872,683 B2 | 1/2018 | Hopkins | |
| 10,172,615 B2* | 1/2019 | Marczyk | A61B 17/07207 |
| 10,349,941 B2 | 7/2019 | Marczyk et al. | |
| 10,548,599 B2* | 2/2020 | Marczyk | A61B 17/068 |
| 11,045,267 B2* | 6/2021 | Hussain | A61B 17/3423 |
| 2001/0044656 A1* | 11/2001 | Williamson, IV | A61B 17/0469 623/2.11 |
| 2002/0047035 A1* | 4/2002 | Coleman | A61B 17/0684 227/175.1 |
| 2002/0117534 A1* | 8/2002 | Green | A61B 17/0684 227/176.1 |
| 2004/0006372 A1 | 1/2004 | Racenet et al. | |
| 2004/0108357 A1 | 6/2004 | Milliman et al. | |
| 2004/0199180 A1 | 10/2004 | Knodel et al. | |
| 2004/0199181 A1 | 10/2004 | Knodel et al. | |
| 2004/0232201 A1 | 11/2004 | Wenchell et al. | |
| 2004/0243151 A1 | 12/2004 | Demmy et al. | |
| 2004/0267310 A1 | 12/2004 | Racenet et al. | |
| 2005/0006429 A1 | 1/2005 | Wales et al. | |
| 2005/0103819 A1 | 5/2005 | Racenet et al. | |
| 2005/0216055 A1 | 9/2005 | Scirica et al. | |
| 2006/0049229 A1 | 3/2006 | Milliman et al. | |
| 2006/0108393 A1* | 5/2006 | Heinrich | A61B 17/115 227/179.1 |
| 2006/0180634 A1 | 8/2006 | Shelton et al. | |
| 2006/0235469 A1* | 10/2006 | Viola | A61B 17/0643 606/219 |
| 2006/0289602 A1 | 12/2006 | Wales et al. | |
| 2007/0073341 A1 | 3/2007 | Smith et al. | |
| 2007/0084897 A1 | 4/2007 | Shelton et al. | |
| 2007/0102472 A1 | 5/2007 | Shelton | |
| 2007/0106317 A1 | 5/2007 | Shelton et al. | |
| 2007/0119901 A1 | 5/2007 | Ehrenfels et al. | |
| 2007/0131732 A1* | 6/2007 | Holsten | A61B 17/115 227/179.1 |
| 2007/0145096 A1 | 6/2007 | Viola et al. | |
| 2007/0170225 A1 | 7/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0179528 A1 | 8/2007 | Soltz et al. | |
| 2007/0194079 A1 | 8/2007 | Hueil et al. | |
| 2007/0194082 A1 | 8/2007 | Morgan et al. | |
| 2007/0244351 A1* | 10/2007 | Wazer | A61N 5/1027 600/3 |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0078802 A1 | 4/2008 | Hess et al. | |
| 2008/0082124 A1 | 4/2008 | Hess et al. | |
| 2008/0110961 A1 | 5/2008 | Voegele et al. | |
| 2008/0169328 A1 | 7/2008 | Shelton | |
| 2008/0169332 A1 | 7/2008 | Shelton et al. | |
| 2008/0169333 A1 | 7/2008 | Shelton et al. | |
| 2008/0287987 A1 | 11/2008 | Boyden et al. | |
| 2008/0296346 A1 | 12/2008 | Shelton, IV et al. | |
| 2008/0308602 A1 | 12/2008 | Timm et al. | |
| 2008/0308603 A1 | 12/2008 | Shelton et al. | |
| 2009/0001121 A1 | 1/2009 | Hess et al. | |
| 2009/0001130 A1 | 1/2009 | Hess et al. | |
| 2009/0062799 A1* | 3/2009 | Holsten | A61B 17/0644 606/75 |
| 2009/0065552 A1* | 3/2009 | Knodel | A61B 17/115 227/180.1 |
| 2009/0090763 A1 | 4/2009 | Zemlok et al. | |
| 2009/0090766 A1 | 4/2009 | Knodel | |
| 2009/0242610 A1 | 10/2009 | Shelton, IV et al. | |
| 2009/0255974 A1 | 10/2009 | Viola | |
| 2009/0255976 A1 | 10/2009 | Marczyk et al. | |
| 2009/0255978 A1 | 10/2009 | Viola et al. | |
| 2009/0272783 A1 | 11/2009 | Crainich | |
| 2009/0272787 A1 | 11/2009 | Scirica | |
| 2009/0277946 A1 | 11/2009 | Marczyk | |
| 2009/0277948 A1 | 11/2009 | Beardsley et al. | |
| 2009/0277949 A1 | 11/2009 | Viola et al. | |
| 2009/0281554 A1 | 11/2009 | Viola | |
| 2009/0283568 A1 | 11/2009 | Racenet et al. | |
| 2009/0302092 A1 | 12/2009 | Kasvikis | |
| 2009/0308907 A1 | 12/2009 | Nalagatla et al. | |
| 2010/0012703 A1 | 1/2010 | Calabrese et al. | |
| 2010/0069942 A1 | 3/2010 | Shelton, IV | |
| 2010/0127041 A1 | 5/2010 | Morgan et al. | |
| 2010/0133317 A1 | 6/2010 | Shelton, IV et al. | |
| 2010/0147921 A1 | 6/2010 | Olson | |
| 2010/0147922 A1 | 6/2010 | Olson | |
| 2010/0155453 A1 | 6/2010 | Bombard et al. | |
| 2010/0191258 A1* | 7/2010 | Harris | A61B 17/0644 606/144 |
| 2010/0191262 A1 | 7/2010 | Harris et al. | |
| 2010/0193566 A1 | 8/2010 | Scheib et al. | |
| 2010/0224668 A1 | 9/2010 | Fontayne et al. | |

(56) References Cited

U.S. PATENT DOCUMENTS

| | | |
|---|---|---|
| 2010/0237128 A1 | 9/2010 | Miller |
| 2010/0249802 A1 | 9/2010 | May et al. |
| 2010/0252611 A1 | 10/2010 | Ezzat et al. |
| 2010/0301098 A1 | 12/2010 | Kostrzewski |
| 2010/0305552 A1 | 12/2010 | Shelton, IV et al. |
| 2010/0327042 A1* | 12/2010 | Amid ................ A61B 17/0684 227/176.1 |
| 2011/0006099 A1 | 1/2011 | Hall et al. |
| 2011/0006101 A1 | 1/2011 | Hall et al. |
| 2011/0006102 A1 | 1/2011 | Kostrzewski |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0174099 A1* | 7/2011 | Ross ................ A61B 17/072 74/89.32 |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0245578 A1* | 10/2011 | Wazer ................ A61N 5/1027 600/3 |
| 2011/0278343 A1 | 11/2011 | Knodel et al. |
| 2011/0288573 A1 | 11/2011 | Fates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0078050 A1* | 3/2012 | Schwartz ................ A61B 1/267 128/200.26 |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0168487 A1* | 7/2012 | Holsten ................ A61B 17/32 227/176.1 |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193398 A1 | 8/2012 | Williams et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Mdridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0289762 A1* | 11/2012 | Shariati ............ A61B 17/07292 600/7 |
| 2012/0292369 A1 | 11/2012 | Munro, III et al. |
| 2012/0292719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |

(56) References Cited

U.S. PATENT DOCUMENTS

| | | |
|---|---|---|
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0153628 A1* | 6/2013 | Euteneuer .......... A61B 17/17 227/175.1 |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0175316 A1 | 7/2013 | Thompson et al. |
| 2013/0193188 A1 | 8/2013 | Shelton, IV et al. |
| 2013/0233908 A1* | 9/2013 | Knodel .............. A61B 17/068 227/177.1 |
| 2013/0240595 A1 | 9/2013 | Penna |
| 2013/0277410 A1 | 10/2013 | Fernandez et al. |
| 2013/0334280 A1 | 12/2013 | Krehel et al. |
| 2013/0334281 A1 | 12/2013 | Williams |
| 2014/0001232 A1 | 1/2014 | Cappola et al. |
| 2014/0001233 A1 | 1/2014 | Cappola et al. |
| 2014/0008413 A1* | 1/2014 | Williams .......... A61B 17/1155 227/179.1 |
| 2014/0014704 A1 | 1/2014 | Onukuri et al. |
| 2014/0014707 A1 | 1/2014 | Onukuri et al. |
| 2014/0021239 A1* | 1/2014 | Kostrzewski .......... A61B 90/08 227/175.3 |
| 2014/0021242 A1 | 1/2014 | Hodgkinson et al. |
| 2014/0025046 A1 | 1/2014 | Williams et al. |
| 2014/0027492 A1 | 1/2014 | Williams |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0103092 A1 | 4/2014 | Kostrzewski et al. |
| 2014/0110453 A1 | 4/2014 | Wingardner et al. |
| 2014/0110455 A1 | 4/2014 | Ingmanson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0142379 A1* | 5/2014 | Faehndrich .......... A61B 18/148 606/41 |
| 2014/0144968 A1* | 5/2014 | Shelton, IV ..... A61B 17/07292 227/175.1 |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203061 A1 | 7/2014 | Hodgkinson |
| 2014/0203062 A1 | 7/2014 | Viola |
| 2014/0203063 A1 | 7/2014 | Hessler et al. |
| 2014/0213848 A1* | 7/2014 | Moskowitz .......... A61B 17/29 600/106 |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239042 A1 | 8/2014 | Simms et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263537 A1 | 9/2014 | Leimbach et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1* | 9/2014 | Hopkins .......... A61B 17/07207 227/180.1 |
| 2014/0284371 A1 | 9/2014 | Morgan et al. |
| 2014/0284372 A1 | 9/2014 | Kostrzewski |
| 2014/0291379 A1 | 10/2014 | Schellin et al. |
| 2014/0291380 A1 | 10/2014 | Meaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2014/0367448 A1 | 12/2014 | Cappola |
| 2014/0374465 A1* | 12/2014 | Cole .................. A61B 17/1155 227/177.1 |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0053749 A1 | 2/2015 | Shelton, IV et al. |
| 2015/0054753 A1 | 2/2015 | Morgan et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0157321 A1 | 6/2015 | Zergiebel et al. |
| 2015/0157323 A1* | 6/2015 | Williams .......... A61B 17/105 227/176.1 |

(56) References Cited

U.S. PATENT DOCUMENTS

| | | | |
|---|---|---|---|
| 2015/0173744 A1 | 6/2015 | Shelton, IV et al. | |
| 2015/0173745 A1 | 6/2015 | Baxter, III et al. | |
| 2015/0173746 A1 | 6/2015 | Baxter, III et al. | |
| 2015/0173747 A1 | 6/2015 | Baxter, III et al. | |
| 2015/0173748 A1* | 6/2015 | Marczyk | A61B 17/0644 227/177.1 |
| 2015/0173749 A1 | 6/2015 | Shelton, IV et al. | |
| 2015/0173750 A1 | 6/2015 | Shelton, IV et al. | |
| 2015/0173755 A1 | 6/2015 | Baxter, III et al. | |
| 2015/0173756 A1 | 6/2015 | Baxter, III et al. | |
| 2015/0173760 A1 | 6/2015 | Shelton, IV et al. | |
| 2015/0173761 A1 | 6/2015 | Shelton, IV et al. | |
| 2015/0173762 A1 | 6/2015 | Shelton, IV et al. | |
| 2016/0073855 A1* | 3/2016 | Farr | A61B 1/0057 600/109 |
| 2016/0135806 A1* | 5/2016 | Euteneuer | A61B 17/068 227/175.1 |
| 2016/0345973 A1* | 12/2016 | Marczyk | A61B 17/07207 |
| 2016/0374737 A1* | 12/2016 | Bootwala | A61B 17/7091 606/279 |
| 2017/0172571 A1* | 6/2017 | Thompson | A61B 17/07207 |
| 2017/0181747 A1 | 6/2017 | Kostrzewski | |
| 2018/0059258 A1* | 3/2018 | MacLaughlin | H02J 7/027 |
| 2019/0082932 A1* | 3/2019 | Schoonbaert | A61B 1/00016 |
| 2019/0321042 A1* | 10/2019 | Marczyk | A61B 17/07207 |
| 2021/0177404 A1* | 6/2021 | Vyas | A61B 1/00181 |
| 2021/0177405 A1* | 6/2021 | Vyas | A61B 8/488 |

FOREIGN PATENT DOCUMENTS

| | | |
|---|---|---|
| CN | 101190139 A | 6/2008 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041002 A2 | 12/1981 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2004520154 A | 7/2004 |
| JP | 2005160933 A | 6/2005 |
| JP | 2006501954 A | 1/2006 |
| JP | 2010514505 A | 5/2010 |
| JP | 2012515631 A | 7/2012 |
| JP | 2013244401 A | 12/2013 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 02098302 A1 | 12/2002 |
| WO | 2004/032760 A2 | 4/2004 |
| WO | 2004032762 A1 | 4/2004 |
| WO | 2009071070 A2 | 6/2009 |
| WO | 2014008289 A2 | 1/2014 |

OTHER PUBLICATIONS

European Search Report dated Oct. 12, 2016, issued in European Application No. 16171477.

European Search Report dated Jan. 16, 2017, issued in EP Application No. 16171477.

Australian Office Action dated Oct. 9, 2020, issued in AU Appln. No. 2016203151, 4 pages.

Japanese Office Action dated Mar. 4, 2020, issued in JP Appln. No. 2016-103162, 10 pages.

* cited by examiner

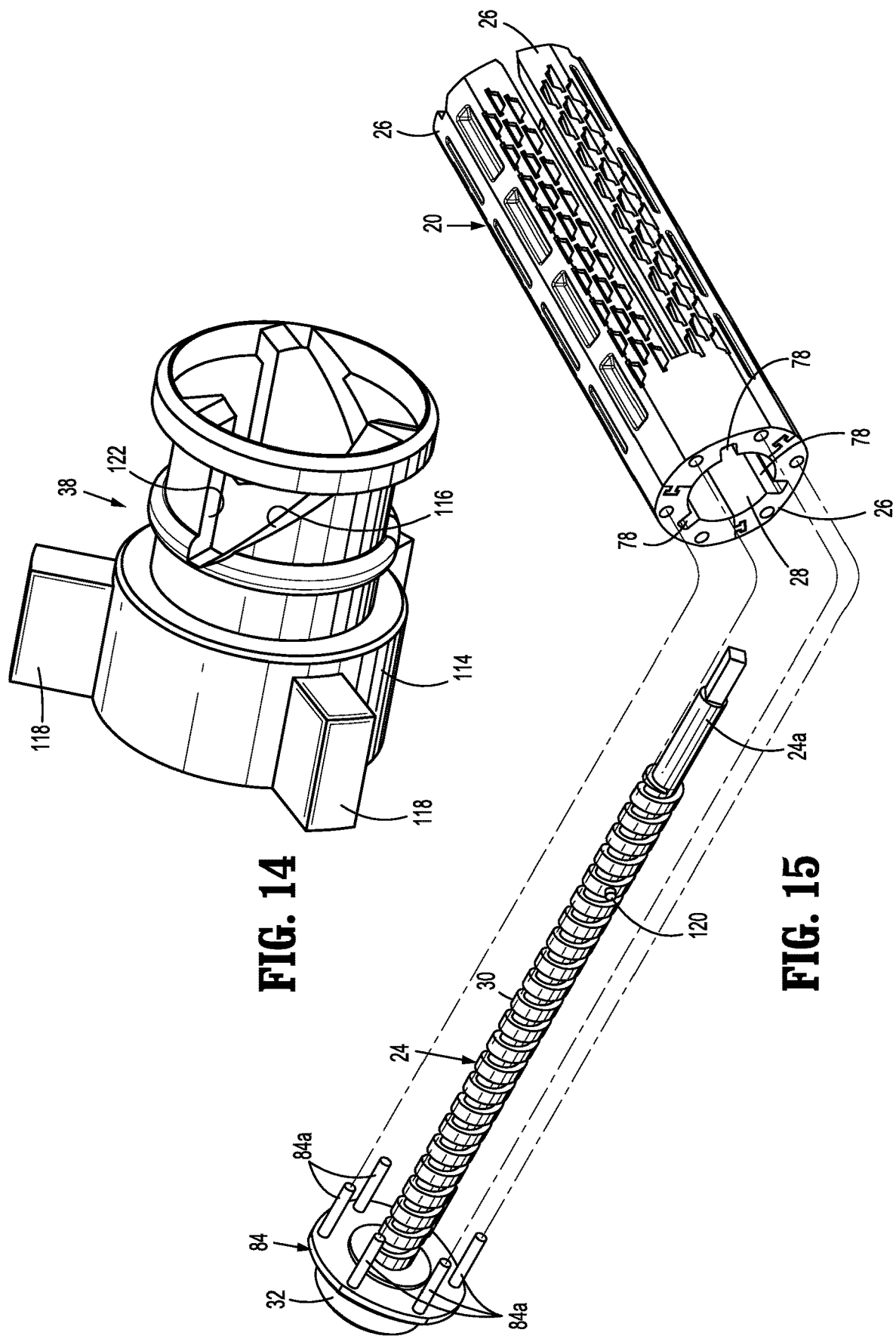

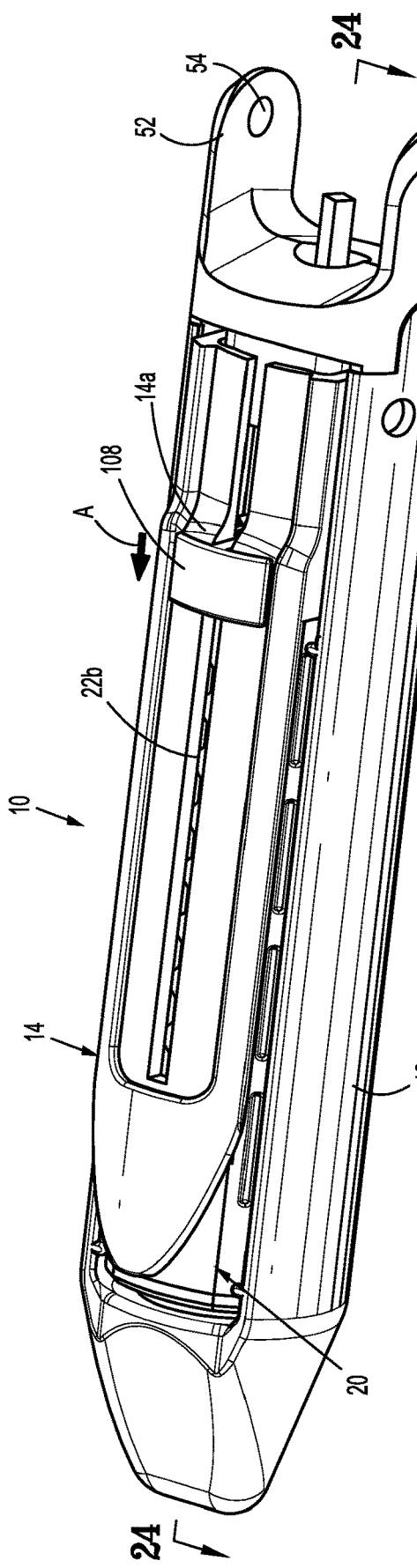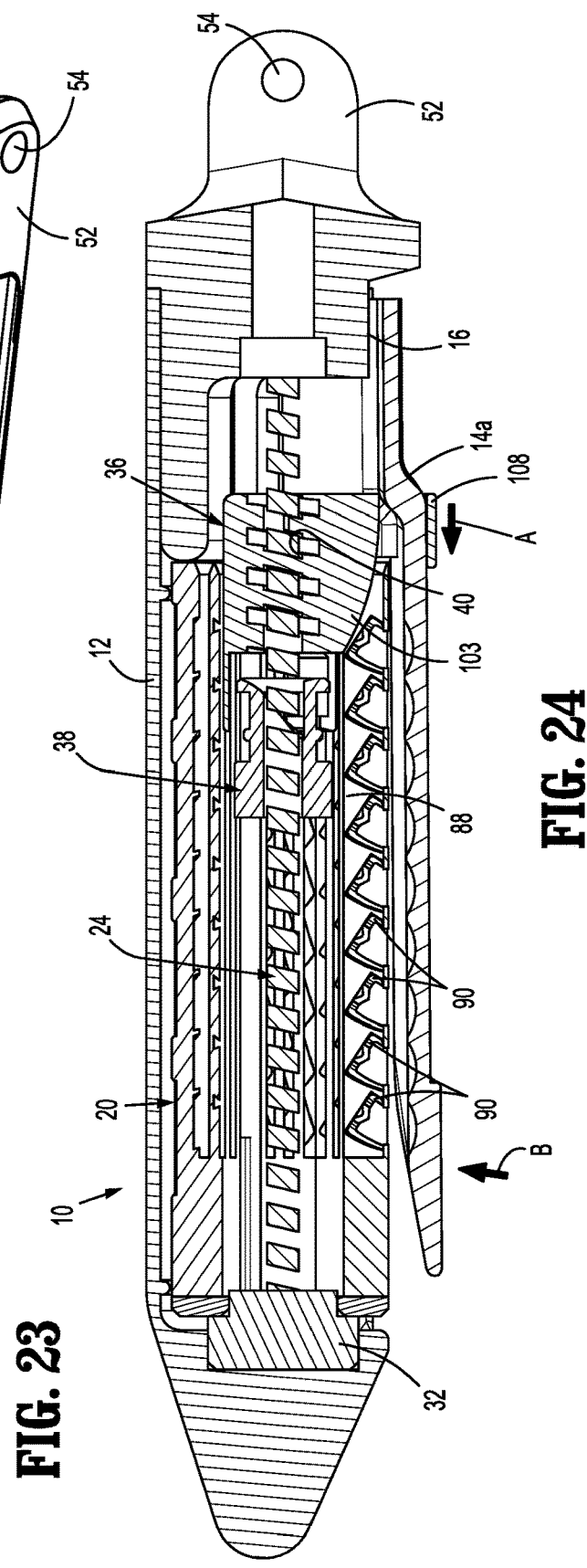

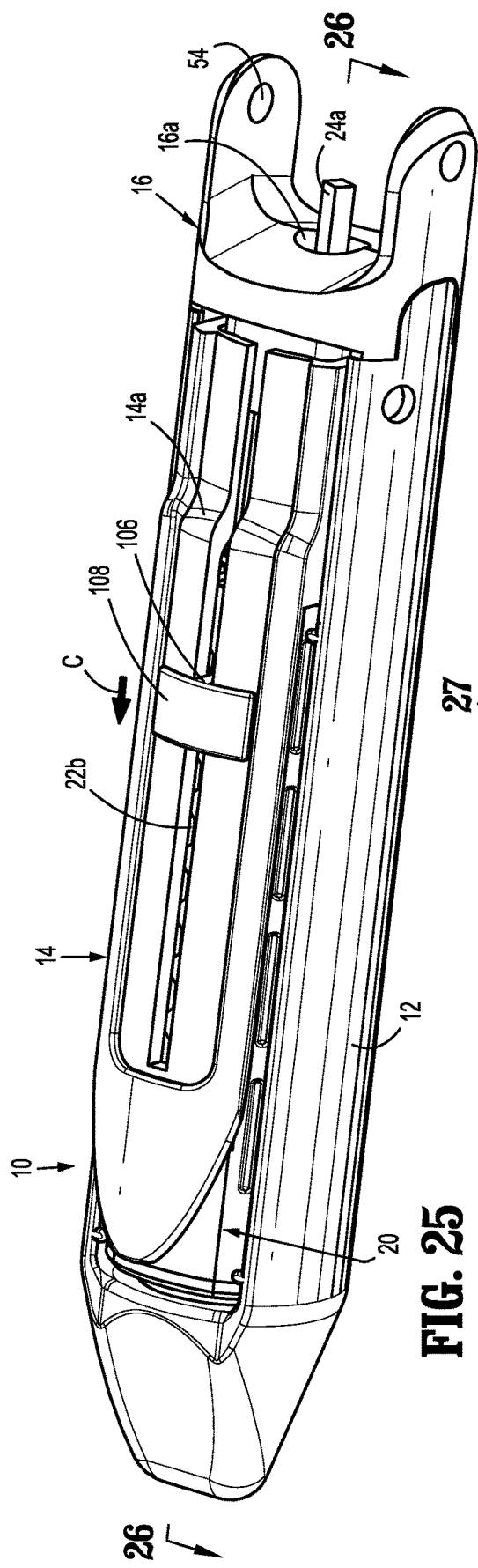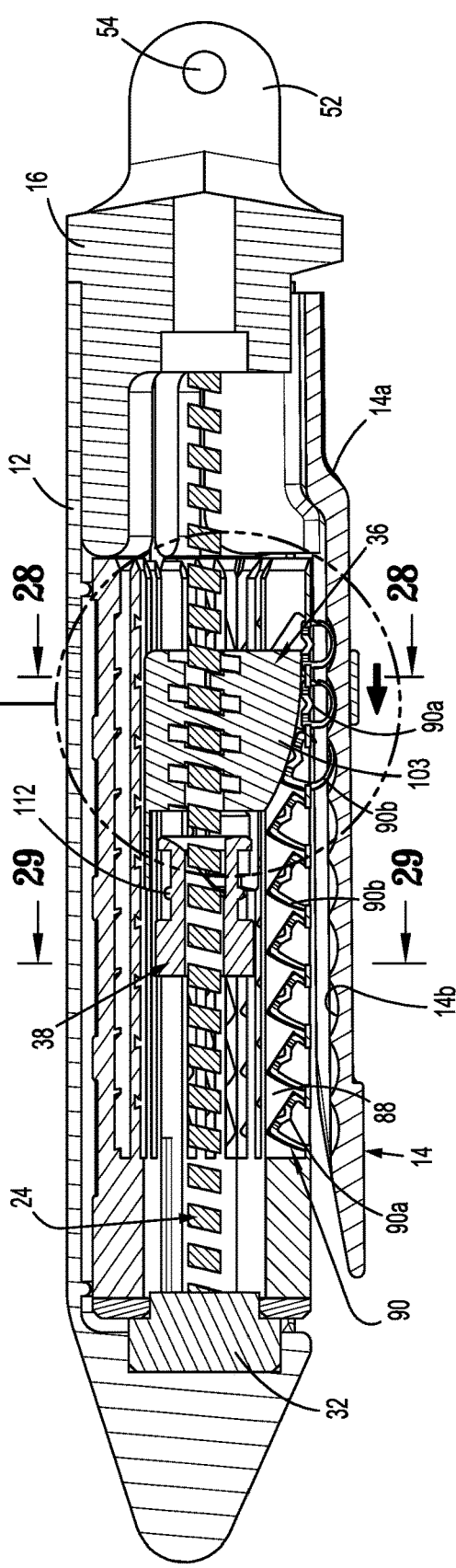
FIG. 25
FIG. 26

MULTI-FIRE LEAD SCREW STAPLING DEVICE

CROSS-REFERENCE TO RELATED APPLICATIONS

This application is a continuation U.S. application Ser. No. 15/150,611 filed May 10, 2016, which claims the benefit of and priority to U.S. Provisional Patent Application No. 62/166,979 filed May 27, 2015, the entire disclosure of which is incorporated by reference herein.

BACKGROUND

Technical Field

The present disclosure relates generally to a surgical stapling device for applying surgical fasteners to body tissue. More particularly, the present disclosure relates to a endoscopic surgical stapling device having a plurality of staple cartridges that are sequentially moved into alignment with an anvil assembly to allow a clinician to fire the stapling device a plurality of times without removing the stapling device from the surgical site.

Background of Related Art

Surgical stapling devices for joining tissue sections are commonly used in surgical procedures. The use of surgical stapling devices as compared to traditional stitching techniques reduces the time required to join and/or cut tissue, thus, reducing the time required to perform a surgical procedure. Reducing the time required to perform a surgical procedure minimizes the time a patient must be anesthetized and, thus minimizes trauma to the patient.

During endoscopic or laparoscopic procedures in which surgery is performed through small incisions or through narrow cannulas inserted through the small incisions in the skin, replacement of the staple cartridge or the loading unit after firing requires removal of the surgical stapling device from the incision or cannula, replacement of the staple cartridge and/or loading unit and reinsertion of the surgical stapling device into the incision or cannula. Removal of the surgical stapling device from the incision for cartridge or loading unit replacement increases the time required to perform the surgical procedure.

It would be advantageous to provide a staple cartridge or loading unit that is capable of being fired a plurality of times before replacement of the staple cartridge or loading unit is required.

SUMMARY

The present disclosure provides, in one aspect, a surgical stapling device including a housing and a plurality of cartridges which are coupled together to form a barrel that is rotatably supported within the housing. Each of the cartridges defines a plurality of staple pockets that support a plurality of staples. An anvil is pivotally coupled to the housing and is movable in relation to the barrel between an open position and a clamped position. A drive shaft extends through the housing and through the barrel. A pusher is operatively connected to the drive shaft and is configured to translate through the barrel to eject the plurality of staples from the plurality of cartridges in response to actuation of the drive shaft. The barrel is positioned within the housing to align a first one of the plurality of cartridges with the anvil to eject the staples from the first cartridge upon movement of the pusher through a first firing stroke and subsequently rotatable within the housing to align a second one of the plurality of cartridges with the anvil to eject the plurality staples from the second cartridge upon movement of the pusher through a second firing stroke.

In some embodiments, the plurality of cartridges includes three cartridges.

In certain embodiments, the drive shaft defines a helical thread and the pusher defines a threaded bore. The drive shaft extends through the threaded bore of the pusher such that rotatable movement of the drive shaft causes longitudinal movement of the pusher about the drive shaft and through the barrel.

In embodiments, an indexer is supported about the drive shaft at a position distal of the pusher. The indexer is operatively engaged with the barrel and adapted to rotate the barrel after the first firing stroke of the pusher to align the second one of the plurality of cartridges with the anvil.

In some embodiments, the indexer includes a body having a plurality of fins and each of the plurality of cartridges defines a longitudinal channel. Each of the longitudinal channels receives one of the plurality of fins of the indexer to rotatably couple the indexer to the barrel such that rotation of the indexer about the drive shaft causes corresponding rotation of the barrel about the drive shaft.

In certain embodiments, a distal end of the pusher is positioned to engage the indexer such that distal movement of the pusher within the barrel causes distal movement of the indexer within the barrel.

In embodiments, the pusher includes a hub and a plurality of flexible arms that extend distally from the hub. The distal end of each of the flexible arms is positioned to engage the indexer to translate distal movement of the pusher into distal movement of the indexer.

In some embodiments, the indexer includes a body defining an annular rib and the distal end of each of the plurality of flexible arms of the pusher is positioned to engage the annular rib as the pusher is moved distally through the barrel to translate distal movement of the pusher into distal movement of the indexer.

In certain embodiments, each of the flexible arms includes an inwardly extending protrusion. The inwardly extending protrusion is configured to engage and pass over the annular rib when the indexer reaches its distal-most position within the housing as the pusher is moved independently of the indexer to its distal-most position to releasably couple the pusher and the indexer such that proximal movement of the pusher through a retraction stroke causes corresponding proximal movement of the indexer.

In embodiments, the indexer body defines a cam slot and the drive shaft includes a shaft pin. The shaft pin is rotatable with the drive shaft and moves within the cam slot of the indexer during the retraction stroke of the pusher to cause rotation of the indexer and the barrel within the housing.

In some embodiments, the plurality of cartridges is coupled together using dove-tail connectors.

In certain embodiments, the surgical stapling device includes an annular end cap having a plurality of posts and each of the plurality of cartridges includes a distal end defining a blind bore. The blind bores of the plurality of cartridges receive the posts of the end cap to secure the distal ends of the plurality of cartridges together.

In embodiments, a ratchet is supported adjacent to the barrel and is configured to permit rotation of the barrel within the housing in a first direction and prevent rotation of the barrel within the housing in a second direction.

In some embodiments, each of the plurality of cartridges defines a notch that is positioned to receive the ratchet.

In certain embodiments, the pusher includes a clamping member that is positioned to engage the anvil to move the anvil from the open position to the clamped position.

In embodiments, the clamp member includes a vertical strut and a beam. The vertical strut extends radially from a hub of the pusher and the beam is positioned transversely to the vertical strut.

In some embodiments, the vertical strut supports a knife.

In certain embodiments, the pusher includes a plurality of pusher fingers. Each of the plurality of pusher fingers is positioned to translate through respective slots defined by the plurality of cartridges to engage and eject the plurality of staples from the plurality of cartridges.

The present disclosure provides, in another aspect, a surgical staple including a backspan, a first leg having a first length extending from one end of the backspan, and a second leg having a second length extending from the other end of the backspan, wherein the first length is greater than the second length. The first and second legs are positioned within a common plane and the backspan has a central portion offset from the common plane.

In embodiments, the backspan is V-shaped.

In embodiments, the first length is between 2 and 10 times the second length.

In some embodiments, the first length is between 4 and 8 times the second length.

BRIEF DESCRIPTION OF THE DRAWINGS

Various embodiments of the presently disclosed surgical stapling device are described herein with reference to the drawings, wherein:

FIG. 14 is a side perspective view of the indexer of the surgical stapling device shown in FIG. 1;

FIG. 15 is a side perspective view of the drive shaft, end cap, and bearing and barrel of the surgical stapling device shown in FIG. 1 with the barrel separated from the other components;

FIG. 23 is a side perspective view of the surgical stapling device shown in FIG. 1 in the clamped position;

FIG. 24 is a side cross-sectional view taken along section line 24-24 of FIG. 23;

FIG. 25 is a side perspective view of the surgical stapling device shown in FIG. 1 as the surgical stapling device is being fired;

FIG. 26 is a cross-sectional view taken along section line 26-26 of FIG. 25;

DETAILED DESCRIPTION OF EMBODIMENTS

Figure 1:
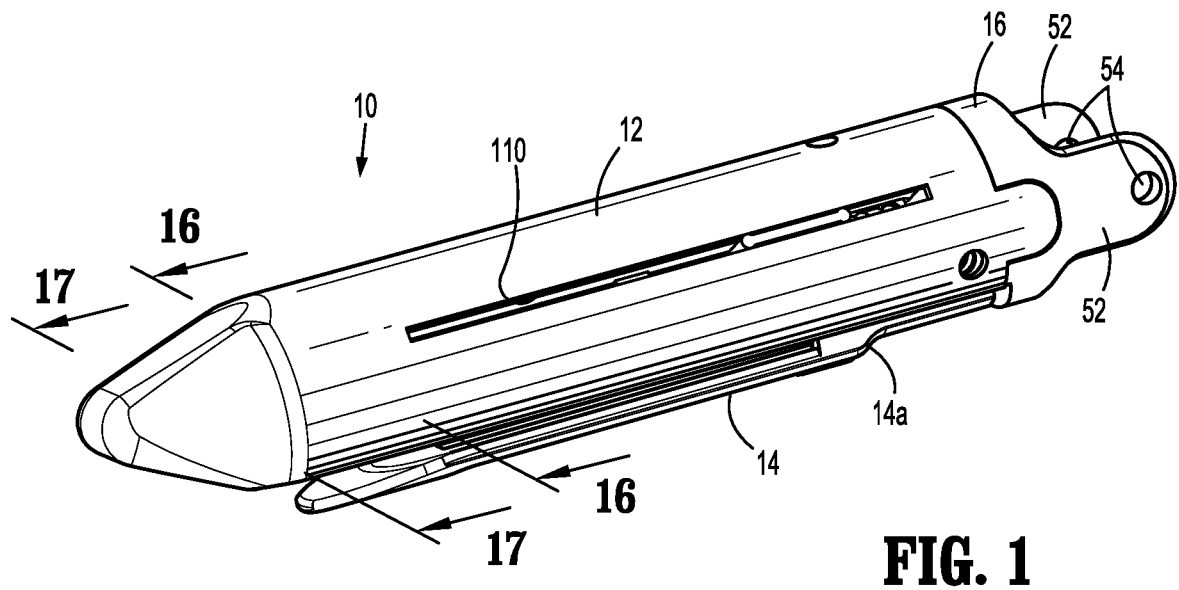
FIG. 1 is a side perspective view from the distal end of one embodiment of the presently disclosed surgical stapling device with the anvil assembly in an clamped position.
Figure 2:
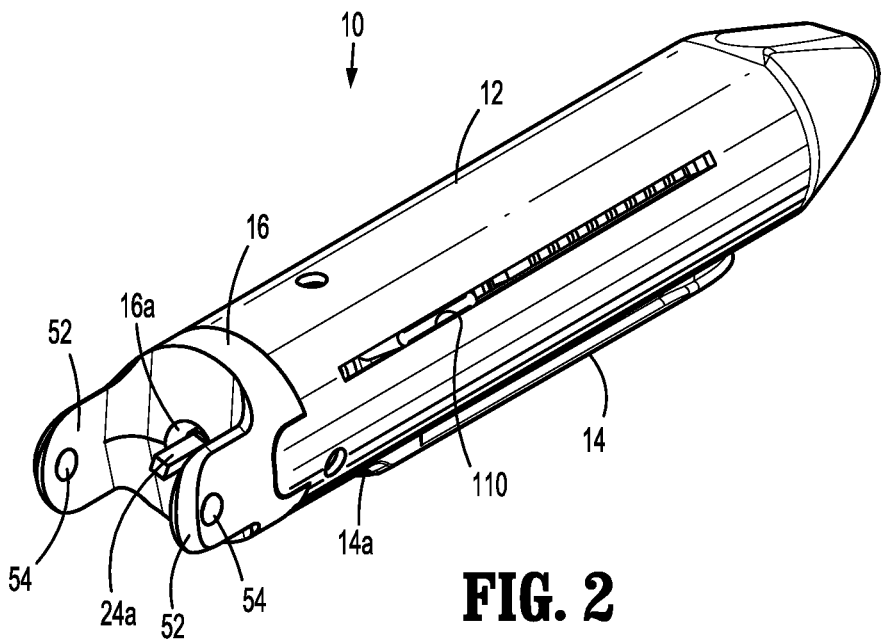
FIG. 2 is a side perspective view from the proximal end of the surgical stapling device shown in FIG. 1.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, the term "endoscopic procedure", as used herein, refers to any procedure performed through a small incision in the skin or through one or more cannulas and encompasses laparoscopic procedures, arthroscopic procedures, etc.

As described in detail below, the presently disclosed surgical stapling device includes a barrel formed by a plurality of cartridges connected to each other that is rotatably supported within a cartridge housing or channel. Each cartridge is sequentially movable into alignment with an anvil and supports an array of staples. A pusher includes a clamping member, a knife and a plurality of pusher fingers that is positioned to engage the staples supported within each cartridge to eject the staples from each of the cartridges. An indexer is provided to rotate the barrel after each use of the surgical stapling device to position a fresh cartridge in alignment with the anvil to facilitate refiring of the stapling device.

FIGS. 1-4 illustrate one embodiment of the presently disclosed surgical stapling device shown generally as 10. The surgical stapling device 10 includes a channel or housing 12, an anvil 14, and a first clevis 16. The housing 12 defines a chamber 18 (FIG. 16) which is dimensioned to rotatably receive a cylindrical barrel 20 as described in detail below. The first clevis 16 has a distal end secured within a proximal end of the chamber 18 and a proximal end adapted to engage a drive mechanism 21 (FIG. 7), such as a manually powered handle assembly, or a powered or robotic drive mechanism. The proximal end of the first clevis 16 defines slots 17 (FIG. 3) that are described in further detail below. In one embodiment, the first clevis 16 is secured to the housing 12 with rivets or pins (not shown). Alternately, other fastening techniques can be used to connect the first clevis 16 to the housing 12, e.g., welding, crimping, etc. The first clevis 16 defines a proximally facing opening 16a (FIG. 2) that receives a proximal end 24a of a drive shaft 24 (FIG. 5).

The anvil 14 has a proximal end defining cam surface 14a and a pair of spaced flanges 22. The cam surface 14a is provided to facilitate movement of the anvil 14 from an open position to a clamped position as described in detail below. Each of the spaced flanges 22 defines an opening 22a that receives a pivot pin (not shown) to pivotally secure the anvil 14 to the housing 12. The anvil 14 also defines a knife slot 22b.

Figure 5:
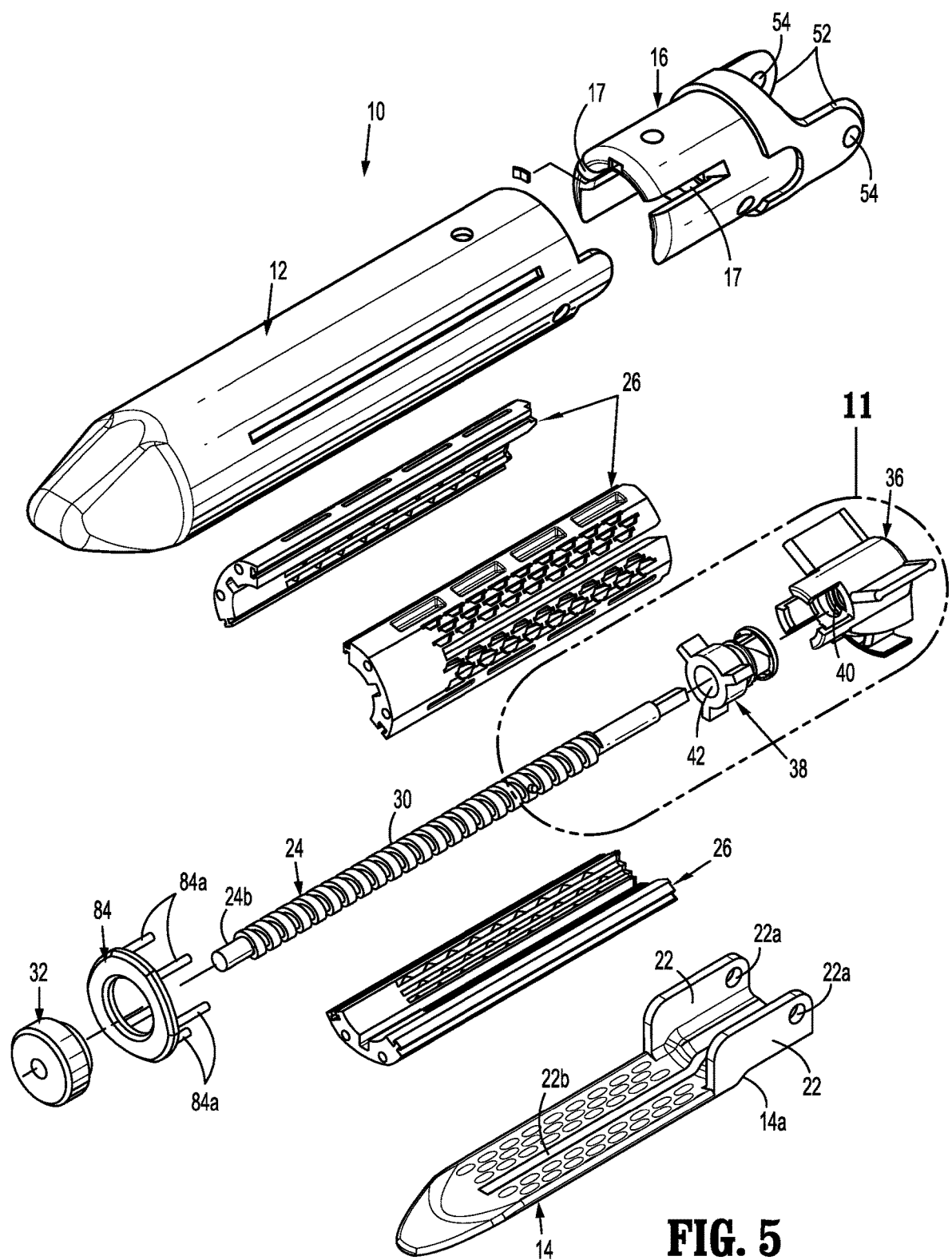
FIG. 5 is an exploded perspective view of the surgical stapling device shown in FIG. 1.

Referring also to FIG. 5, the cylindrical barrel 20 (FIG. 3) is formed from a plurality of cartridges 26 that are connected together to define a bore 28 (FIG. 15) that extends the length of the cylindrical barrel 20. Although three cartridges 26 are shown, it is envisioned that the barrel 20 can be formed from two or more cartridges 26, e.g., 2, 4, 5, etc. The drive shaft 24 defines a helical thread 30 and has a distal end 24b (FIG. 5) positioned adjacent the distal end of the housing 12. A bearing 32 is supported in the distal end of the housing 12 and supports the distal end 24b of the drive shaft 24. The proximal end 24a of the drive shaft 24 is unthreaded and is configured to engage the drive mechanism 21 (FIG. 7).

Figure 3:
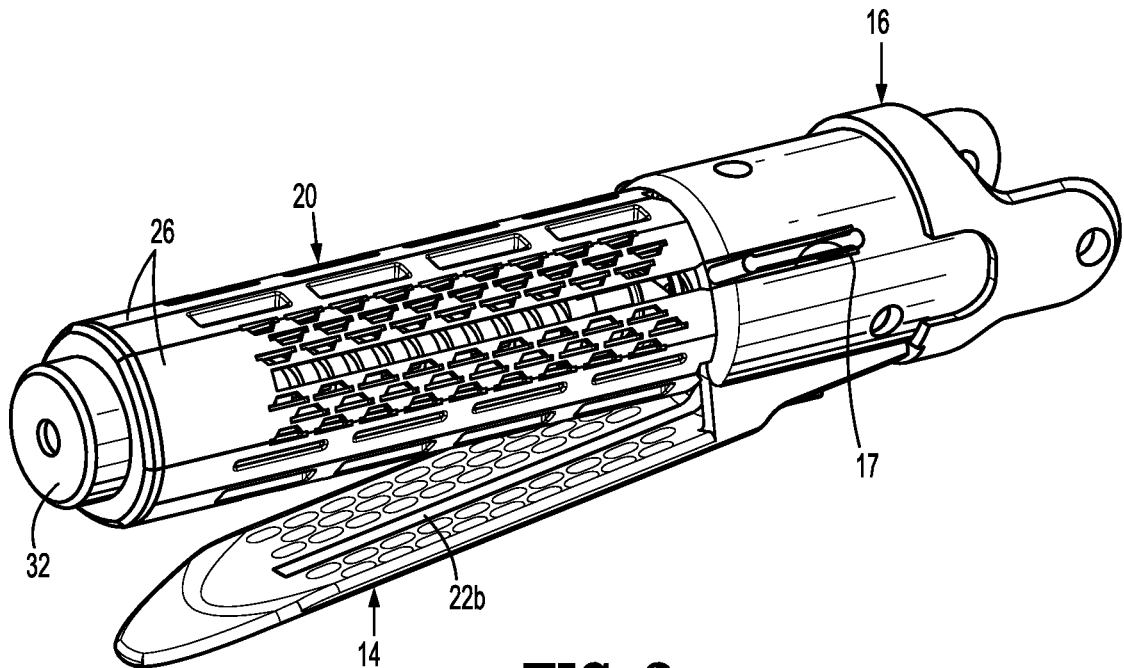
FIG. 3 is a side perspective view of the surgical stapling device shown in FIG. 1 with the housing removed and the anvil assembly in the open position.
Figure 4:
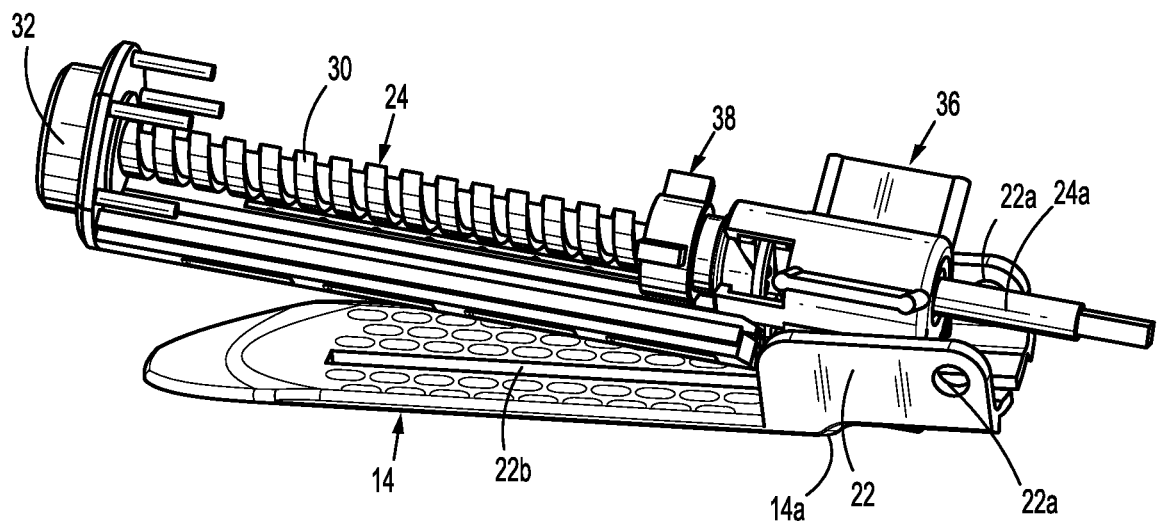
FIG. 4 is a side perspective view of the surgical stapling device shown in FIG. 3 with the housing and barrel removed and the anvil assembly in the open position.

Referring to FIGS. 3-5, the drive shaft 24 supports a pusher 36 and an indexer 38. The pusher 36 defines a threaded longitudinally extending bore 40 (FIG. 5) that is dimensioned to engage the helical thread 30 of the drive shaft 24 such that rotational movement of the drive shaft 24 causes linear movement of the pusher 36 as described in detail below. The indexer 38 is positioned distally of the pusher 36 and also defines a longitudinally extending bore 42 (FIG. 5) that is dimensioned to receive the drive shaft 24. The indexer 38 is positioned distally of the pusher 36 such that distal movement of the pusher 36 causes the indexer 38 to be advanced distally along the drive shaft 24 as described in detail below.

Figure 6:
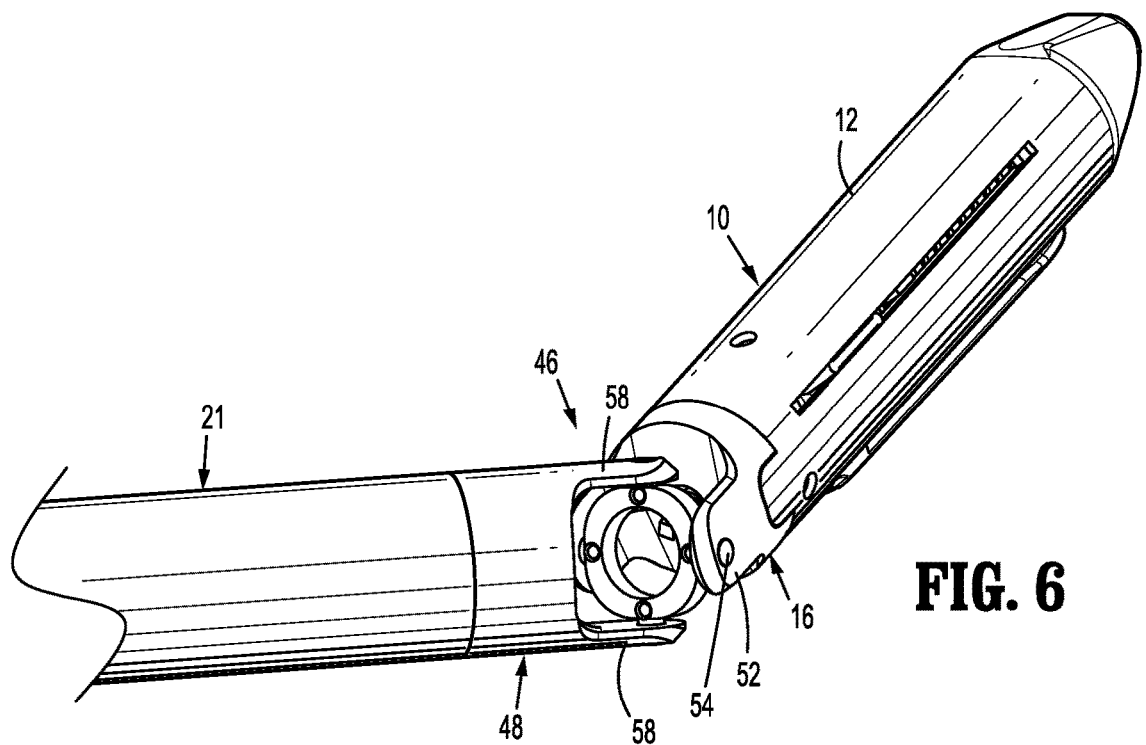
FIG. 6 is a side perspective view from the proximal end of the surgical stapling device shown in FIG. 1 in an articulated position in relation to a supporting shaft.
Figure 7:
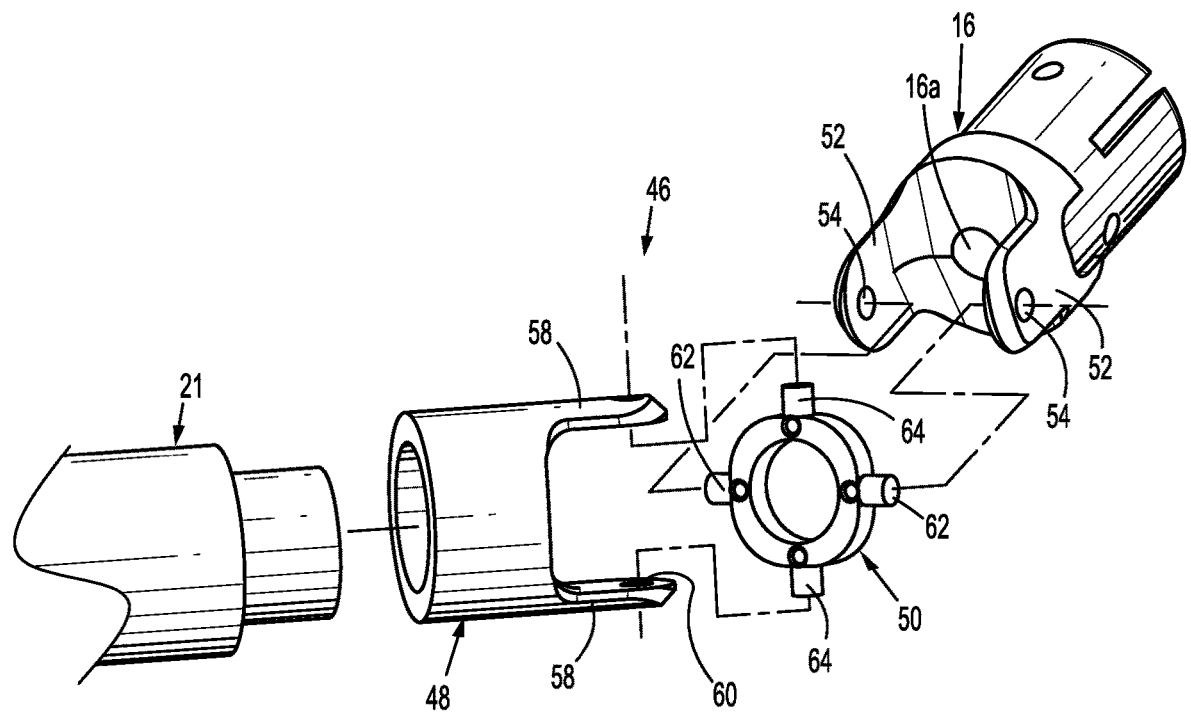
FIG. 7 is a side, exploded, perspective view of the universal joint of the surgical stapling device shown in FIG. 6.

Referring to FIGS. 6 and 7, the first clevis 16 forms a distal portion of the universal joint 46 including a second clevis 48 that is coupled to the first clevis 16 by a swivel mount 50. The first clevis 16 includes a first pair of spaced fingers 52 each defining an opening 54. Similarly, the second clevis 48 includes a second pair of spaced fingers 58 each defining an opening 60. The swivel mount 50 has a first pair of coaxial pivot members 62 and a second pair of coaxial pivot members 64 which are offset ninety degrees from each adjacent one of the first pair of coaxial pivot members 62. The first pair of coaxial pivot members 62 are received in the openings 54 of the first clevis 16 to pivotally secure the surgical stapling device 10 to the swivel mount 50 about a first axis and the second pair of coaxial pivot members 64 are received in the openings 60 of the second clevis 48 to pivotally secure the second clevis 48 to the swivel mount 50 about a second axis transverse to the first axis. The swivel mount 50 of the universal joint 46 can be secured to the drive mechanism by four cables (not shown) that have distal ends connected to the swivel mount 50 at positions ninety degrees offset from each other. The cables can be selectively retracted to pivot the surgical stapling device about the first and/or second axes.

Although a universal joint 46 is described herein to connect the surgical stapling device 10 to the drive mechanism 21, it is envisioned that the surgical stapling device 10 can be coupled to a drive mechanism 21 using a variety a coupling techniques including, e.g., single axis pivot members, ball joints, etc.

Figure 8:
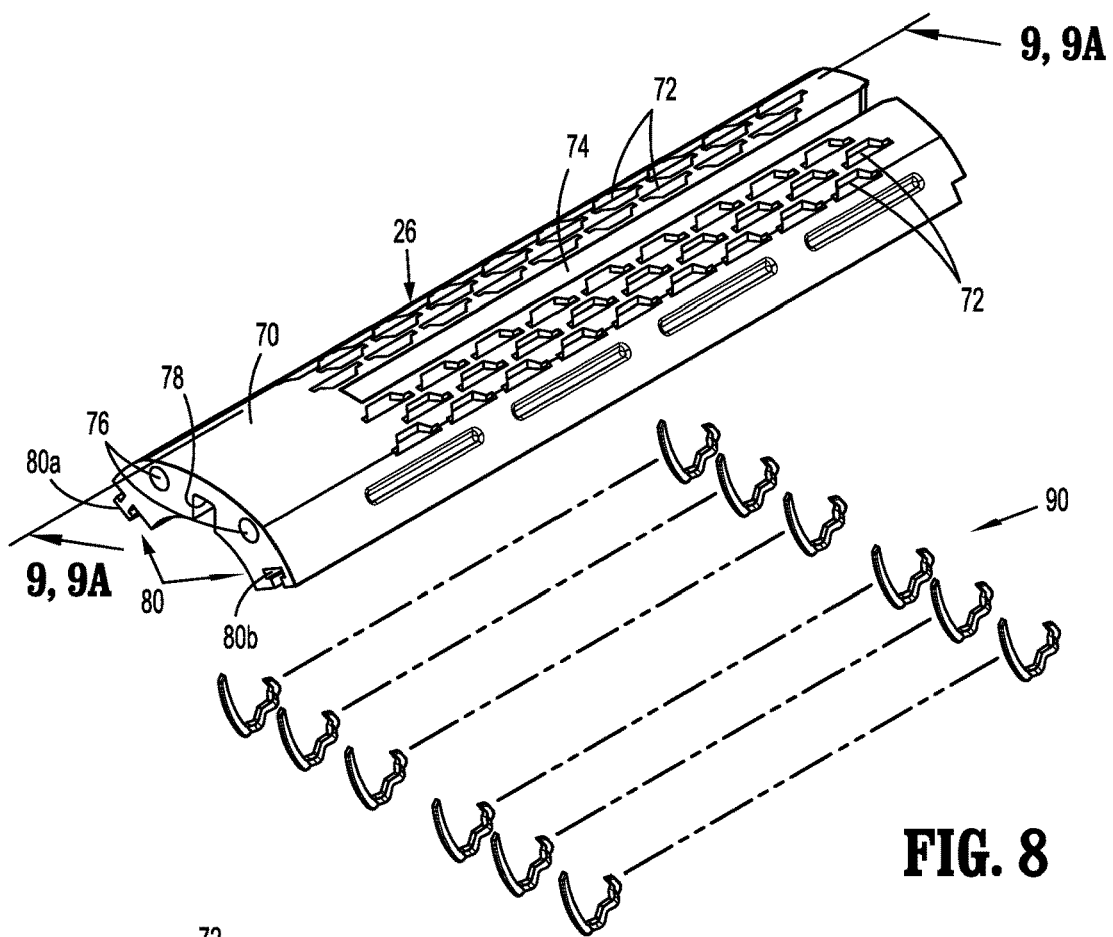
FIG. 8 is a side exploded, perspective view of one of the cartridges of the surgical stapling device shown in FIG. 1.
Figure 9:
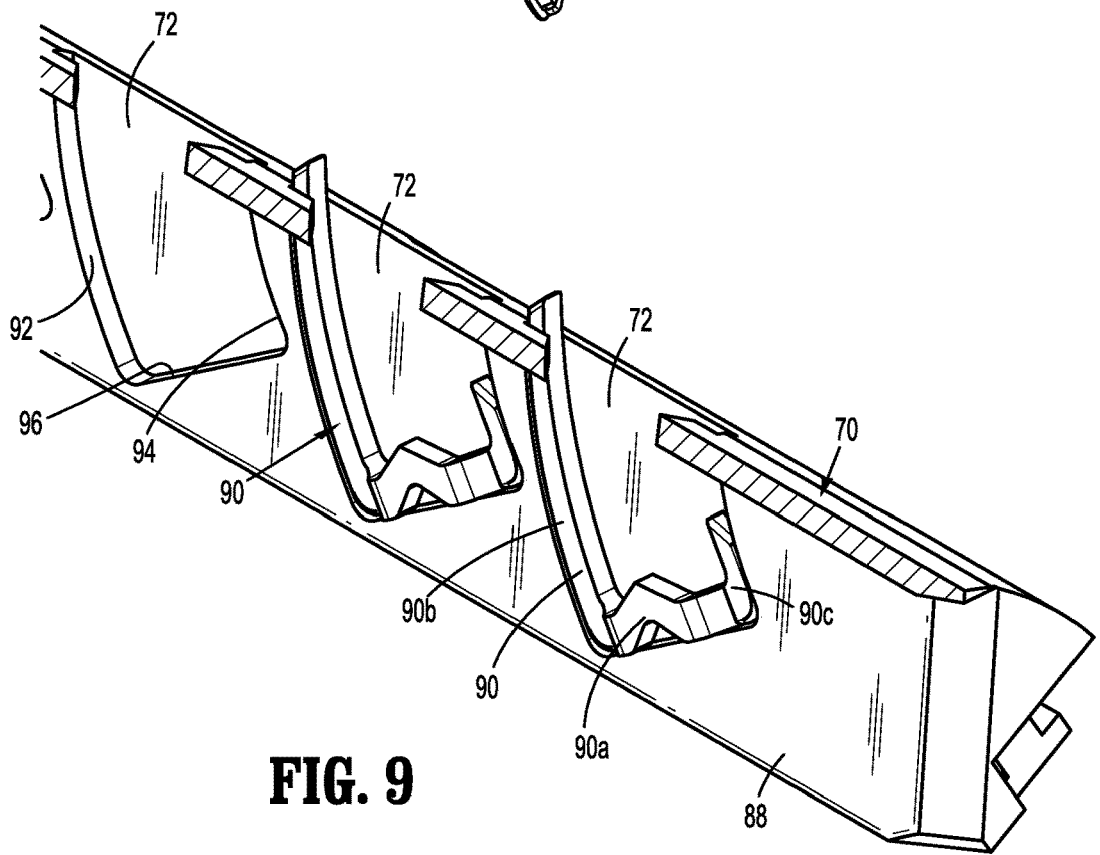
FIG. 9 is a side cross-sectional view through a portion of the cartridge shown in FIG. 8 with the staples positioned in the staple pockets of the cartridge.
Figure 9A:
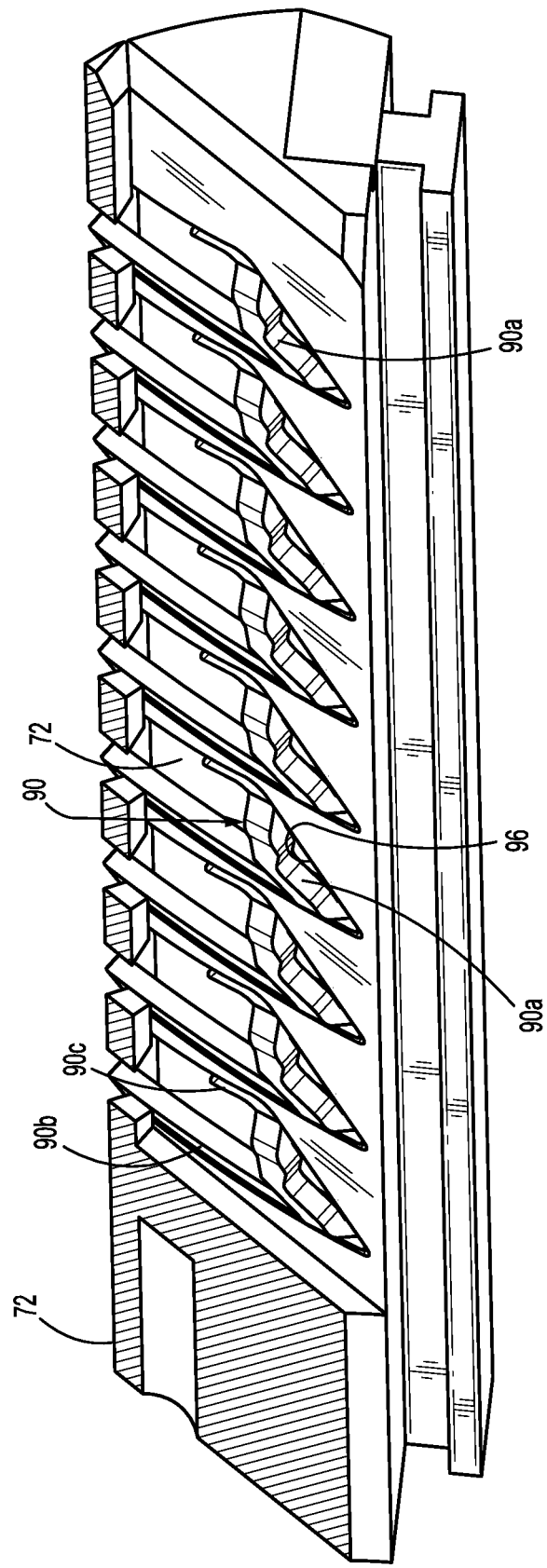
FIG. 9A is a cross-sectional view taken along sectionline 9A-9A of FIG. 8.
Figure 10:
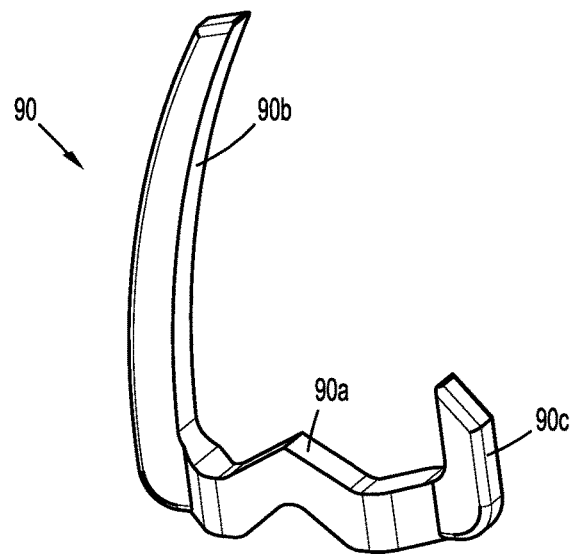
FIG. 10 is a side perspective view of one of the staples of the cartridge assembly shown in FIG. 8.
Figure 11:
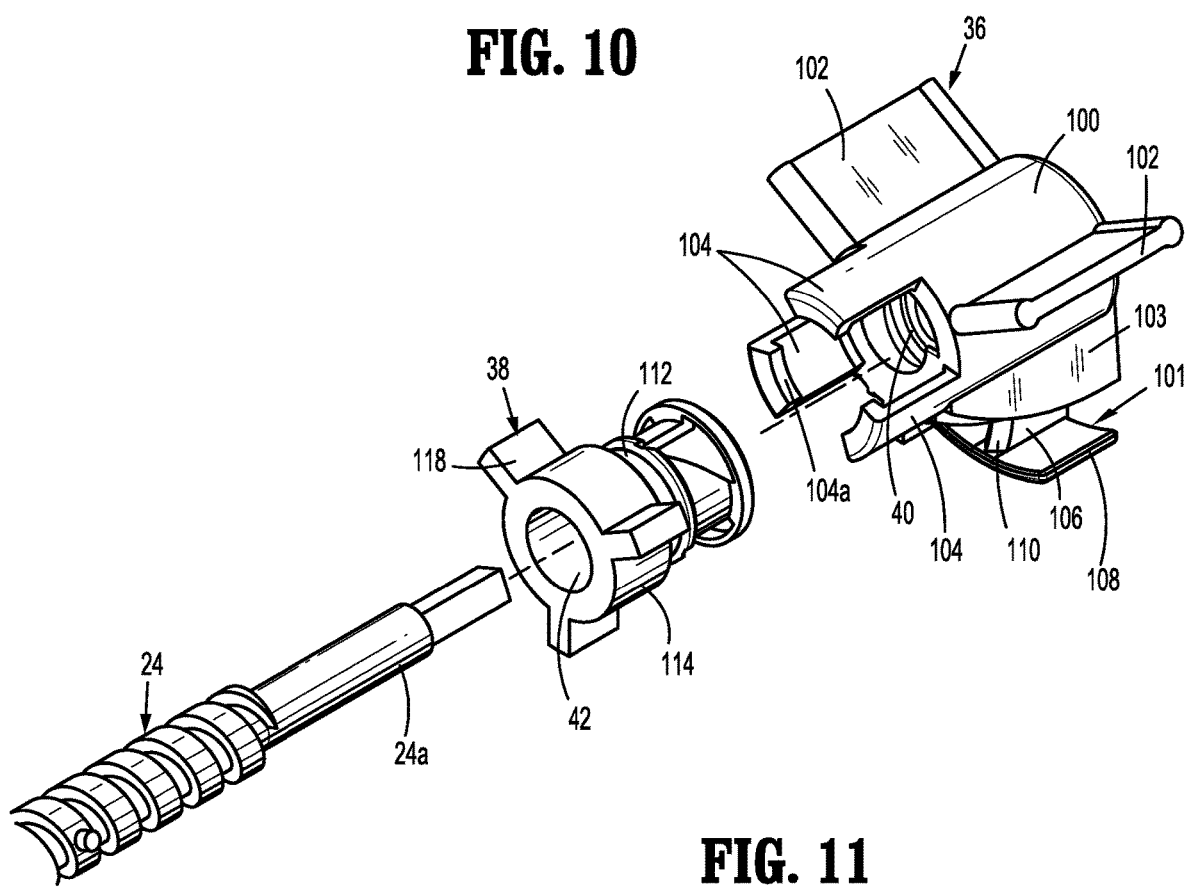
FIG. 11 is a side exploded, perspective view of the drive shaft, indexer and pusher of the surgical stapling device shown in FIG. 1.
Figure 12:
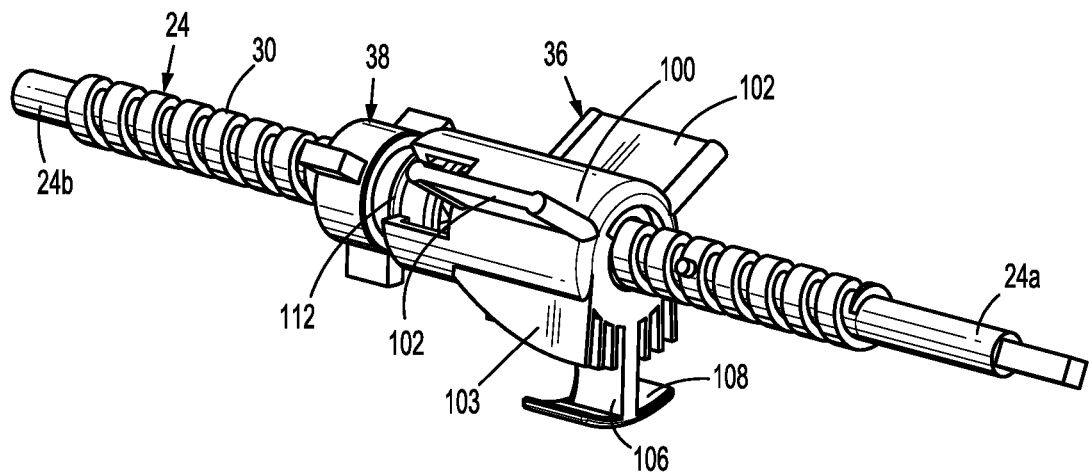
FIG. 12 is a side perspective view of the drive shaft, indexer and pusher of the surgical stapling device shown in FIG. 11 with the components assembled.
Figure 13:
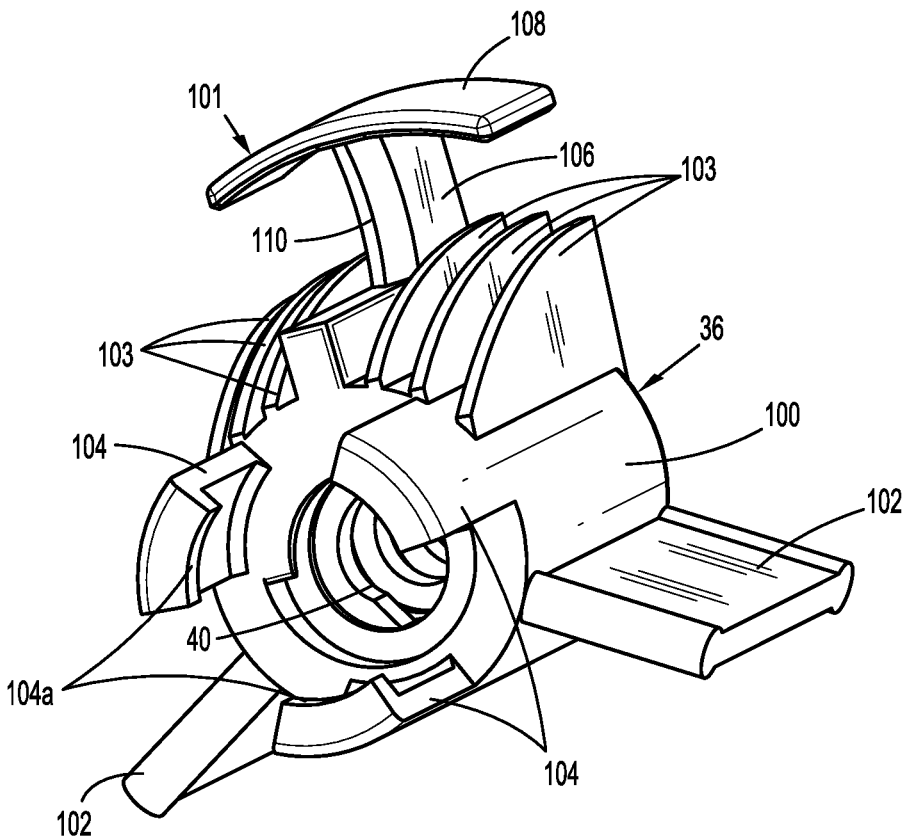
FIG. 13 is a perspective view from the distal end of the pusher of the surgical stapling device shown in FIG. 1.

Referring to FIGS. 8-10, each cartridge 26 includes a cartridge body 70 defining a plurality of rows of staple pockets 72 and a knife slot 74. In embodiments, the body 70 defines three linear rows of staple pockets 72 on each side of the knife slot 74. Alternately, the body may define one or more rows of staple pockets 72 on each side of the knife slot 74. Each cartridge body 70 also has a distal end defining two spaced blind bores 76, a longitudinal channel 78 that is aligned with the knife slot 74 and a coupling member 80 positioned on each of the side edges of the cartridge body 70.

Figure 16:
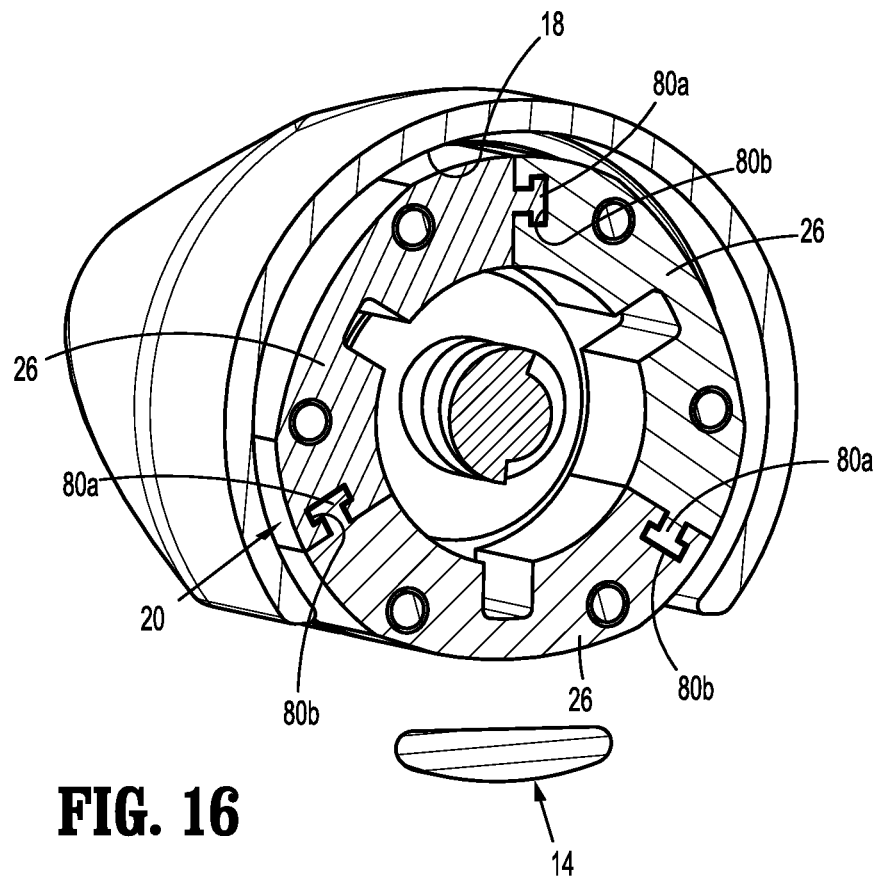
FIG. 16 is a cross-sectional view taken along section line 16-16 of FIG. 1.
Figure 17:
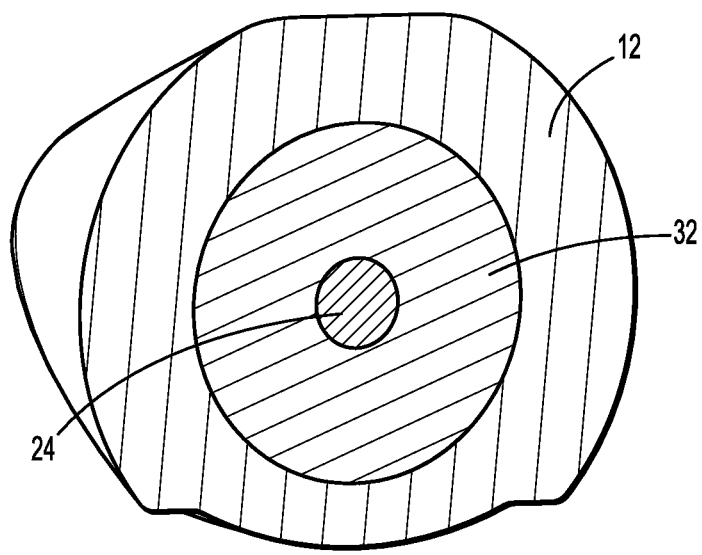
FIG. 17 is a cross-sectional view taken along section line 17-17 of FIG. 1.
Figure 18:
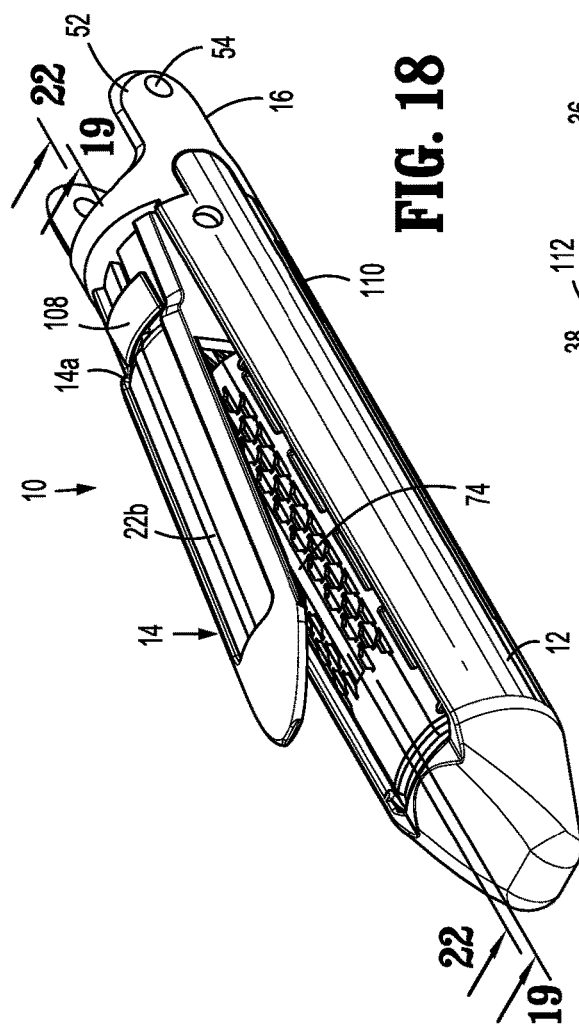
FIG. 18 is a side perspective view of the surgical stapling device shown in FIG. 1 in the open position.
Figure 19:
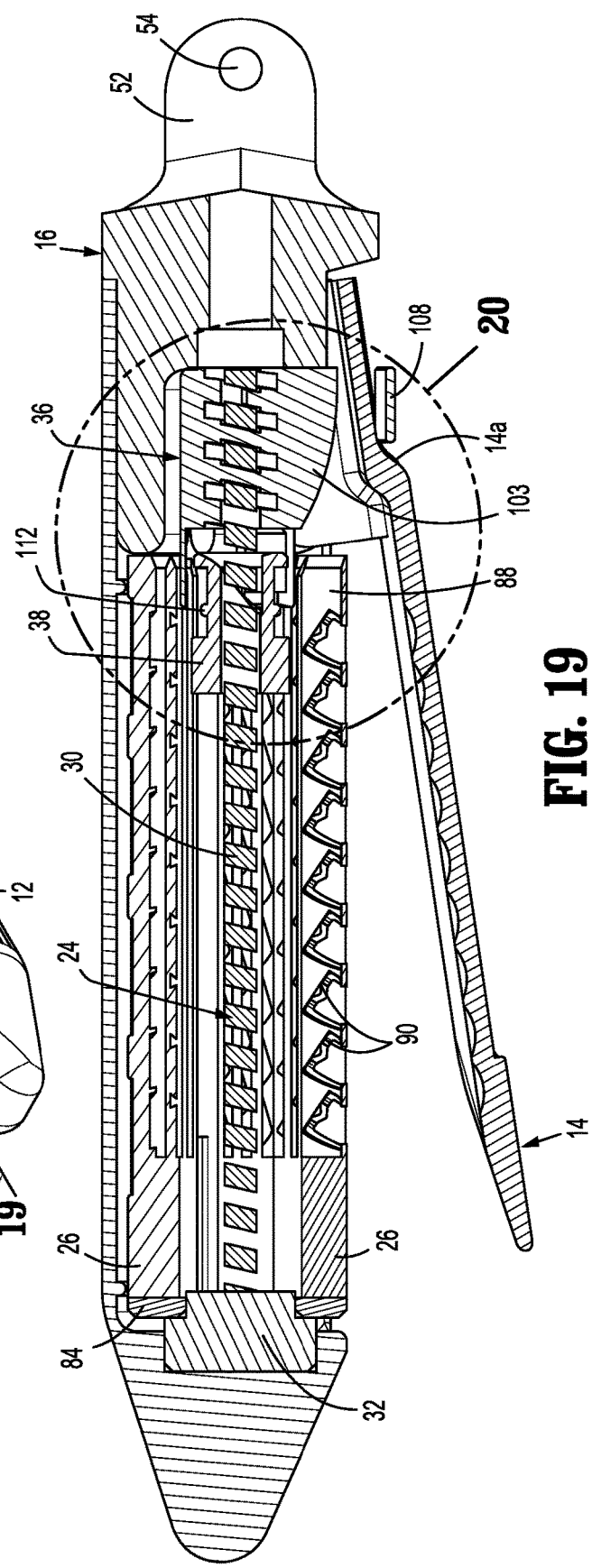
FIG. 19 is a cross-sectional view taken along section line 19-19 of FIG. 18.
Figure 20:
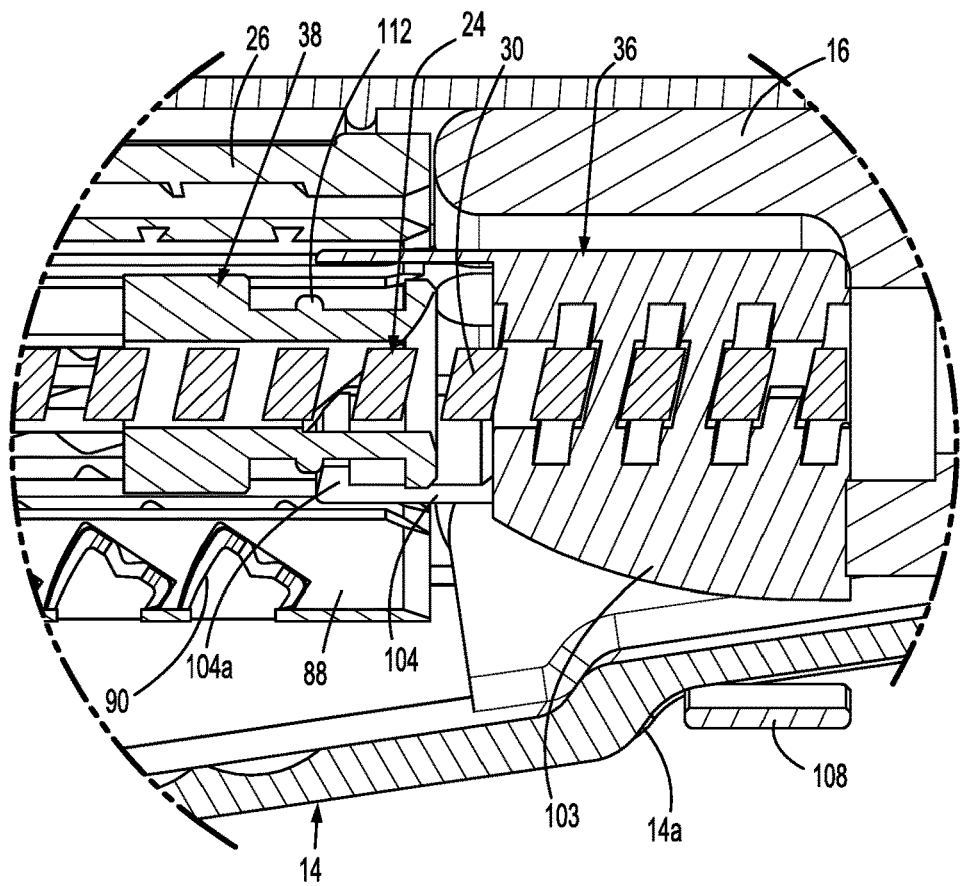
FIG. 20 is an enlarged view of the indicated area of detail shown in FIG. 19.
Figure 21:
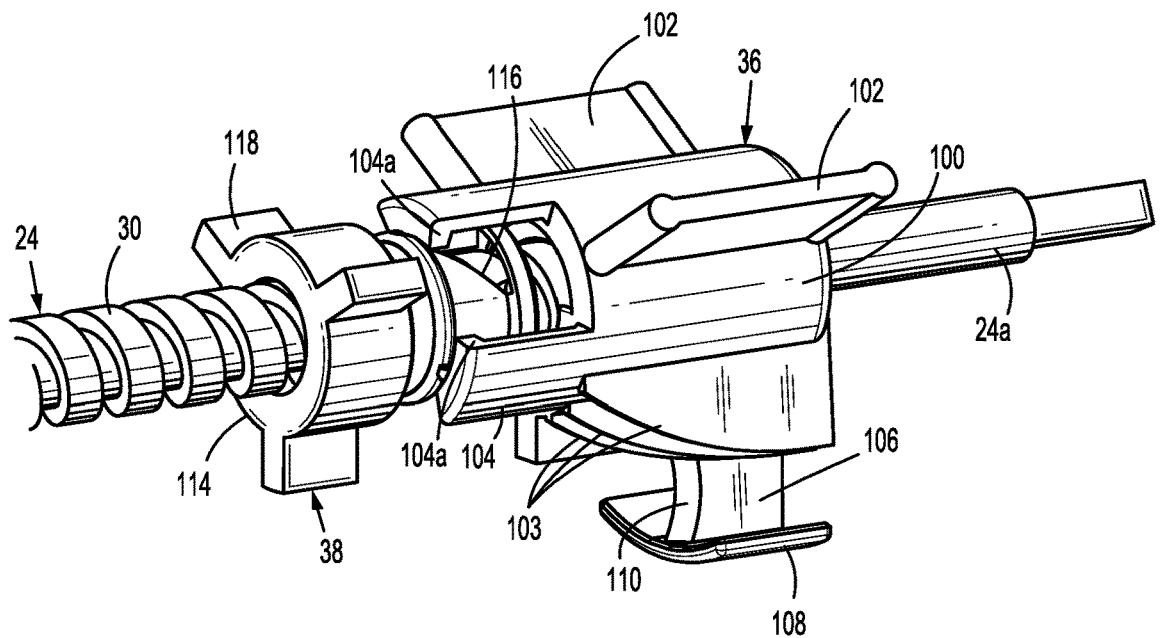
FIG. 21 is a side perspective view of the drive shaft, pusher and indexer of the surgical stapling device shown in FIG. 1 assembled in the start position.
Figure 22:
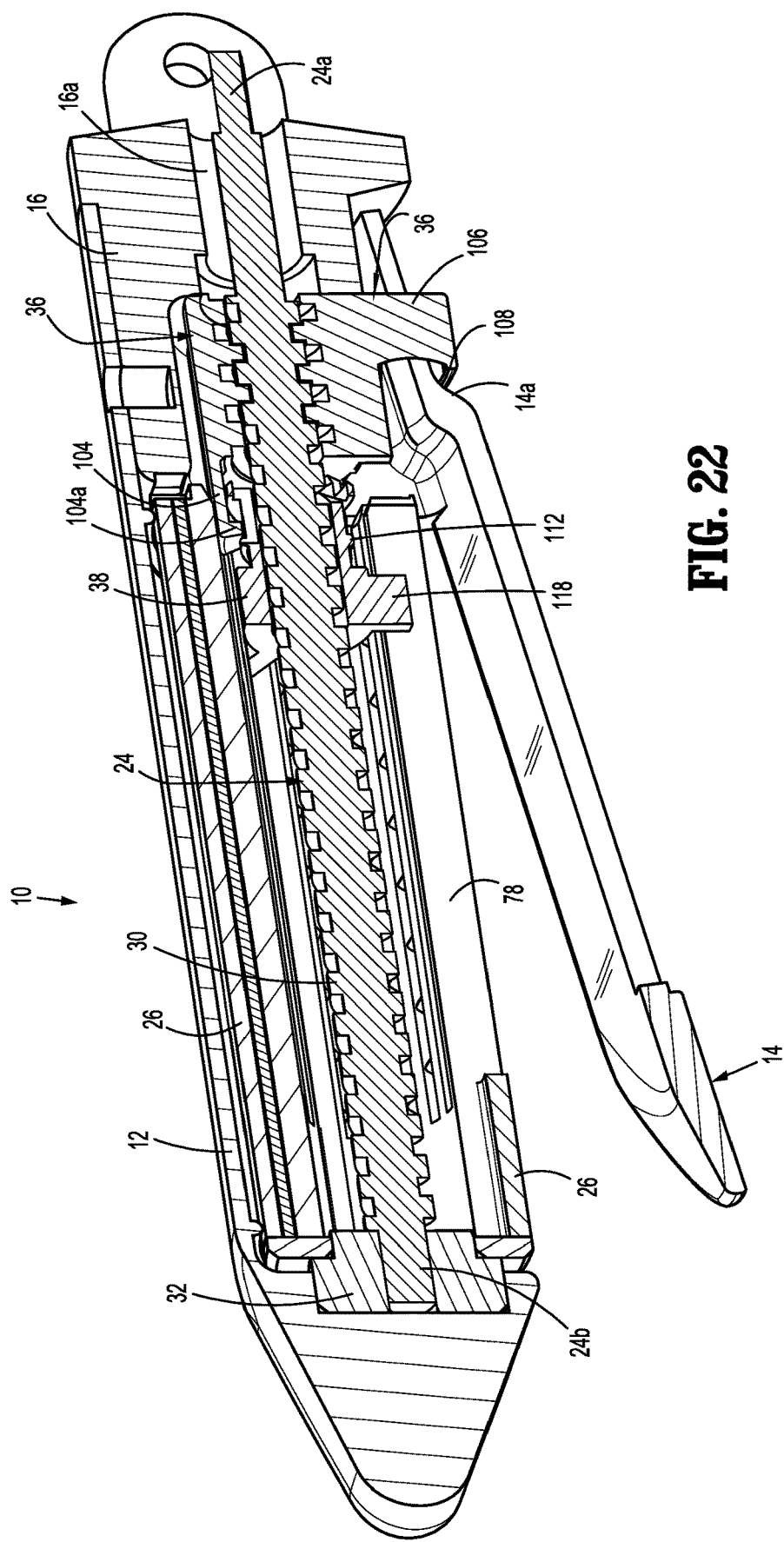
FIG. 22 is a cross-sectional view taken along section line 22-22 of FIG. 18.

In embodiments, the coupling member 80 includes a dovetail projection 80a positioned along one side edge of the cartridge body 70 and a dove-tail groove 80b positioned along an opposite side edge of the cartridge body 70 (FIG. 16). The dove-tail projections 80a and grooves 80b facilitate attachment of each cartridge 26 to adjacent cartridges 26 to define the cylindrical barrel 20 (FIG. 16). The blind bores 76 at the distal end of each cartridge 26 receive the legs 84a of an end cap 84 to further secure the cartridges 26 in a radial and axially fixed position in relation to each other.

Each cartridge body 70 defines a slot 88 (FIG. 9) that is aligned with each row of staples 90. As described above, the staples 90 are supported in one or more rows of staple pockets 72 located on each side of the knife slot 74. In the illustrated embodiment, each cartridge body 70 defines three rows of staples 90 on each side of the knife slot 74 and, thus, defines three slots 88 on each side of the knife slot 74.

Each staple pocket 72 has a curved distal wall 92, a curved proximal wall 94 and angled shelf 96 that extends between the distal and proximal walls 92, 94. Each of the staples 90 includes the backspan 90a, a first leg 90b and a second leg 90c. The shelf 96 supports the backspan 90a of the staple 90. The first leg 90b extends from one end of the backspan 90a and is elongated and curved. When a staple 90 is supported in the staple pocket 72, the first leg 90b is positioned adjacent to the curved distal wall 92 of a respective staple pocket 72. The second leg 90c has a length that is substantially shorter than the length of the first leg 90b and is positioned adjacent the proximal wall 94 of the staple pocket 72. In embodiments, the first leg 90b has a length between 2 and 10 times greater than the length of the second leg 90c. In certain embodiments, the first leg 90b has a length between 4 and 8 times greater than the length of the second leg 90c. The backspan 90a of each staple 90 has a triangular or V-shaped configuration and includes a central portion that is offset from a common plane defined by the first and second legs 90b, 90c of the staple 90. The backspan 90a is configured to extend off the shelf 96 and into a respective slot 88 defined by the cartridge body 70 such that movement of the pusher 36 through the slots 88 of the cartridge body 70 causes the staples 90 to be ejected from the staple pockets 72.

The presently disclosed staple geometry facilitates deformation of the staple 90 from a non-deformed configuration to a deformed or closed configuration (FIG. 27) by deforming only the first, elongated leg 90b towards the shorter leg 90c. This eliminates the need for pushers that engage the backspan of staples, as are conventional in the prior art, to deform the staples. It is envisioned that the second leg 90c may be completely removed from the staple 90.

Referring to FIGS. 11-15, the pusher 36 includes a hub 100 defining the threaded longitudinally extending bore 40, a clamping member 101, wings 102 and a plurality of pusher fingers 103 extending radially outward from the hub 100, and a plurality of flexible arms 104 extending distally from the hub 100. The clamping member 101 has a vertical strut 106 and a horizontal beam 108. A cutting edge or knife 110 is formed or supported on a distal face of the vertical strut 106. The wings 102 and the vertical strut 106 are positioned about the hub 100 of the pusher 36 such that the each of the wings 102 and the vertical strut 106 is slidably received within the knife slot 74 (FIG. 8) of a respective cartridge 26. In addition, each of the wings 102 is dimensioned to extend through an elongated slot 110 (FIG. 1) defined in the housing 12 (FIG. 1) and the slot 17 (FIG. 3) defined in the first clevis 16 (FIG. 5) and the vertical strut 106 of the clamping member 101 is positioned to extend through the knife slot 22b (FIG. 5) of the anvil 14 to prevent the pusher 36 from rotating in relation to the housing 12.

Each of the flexible arms 104 extends distally from the hub 100 of the pusher 36 towards the indexer 38 and includes an inwardly extending projection 104a. The inwardly extending projections 104a are positioned to engage an annular rib 112 formed on the indexer 38 as described in further detail below. Each of the pusher fingers 103 extends radially outward from the hub 100 of the pusher 36 and is slidably received within a respective slot 88 (FIG. 9) of the cartridge body 70. The pusher fingers 103 are positioned to engage the staples 90 to eject the staples 90 from the cartridge body 70 as the pusher 36 is moved through the barrel 20 (FIG. 15) as described in detail below.

The indexer 38 includes a body 114 defining the longitudinally extending bore 42, the annular rib 112 and cam slots 116. The indexer 38 also includes a plurality of fins 118 that extend radially outward from the body 114. The annular rib 112 is positioned distally of and in contact with the projections 104a of the flexible arms 104 of pusher 36 such that distal movement of the pusher 36 within the barrel 20 about the drive shaft 24 causes distal movement of the indexer 38 about the drive shaft 24. When the indexer 38 is advanced to its distal-most position (FIG. 31), the indexer 38 engages the bearing 32 supported at the distal end of the housing 12, to prevent further distal movement of the indexer 38. Further distal movement of the pusher 36 causes the flexible arms 104 of pusher 36 to flex outwardly as the pusher 36 moves distally independently of the indexer 38 such that projections 104a snap over and engage the annular rib 112 formed on the indexer 38 to releasably couple the pusher 36 to the indexer 38. In the coupled position, the indexer body 114 is positioned further proximally in relation to the hub 100 of the pusher 36 such that, upon retraction, the indexer 38 is able to move further proximal within the barrel 20 about the drive shaft 24 as described in further detail below. With the projections 104a of the flexible arms 104 of the pusher 36 engaged with the annular rib 112 of the indexer 38, proximal movement or retraction of the pusher 36 within the barrel 20 will cause corresponding proximal movement of the indexer 38 within the barrel 20.

Each of the plurality of fins 118 of the indexer 38 is received within a longitudinal channel 78 (FIG. 15) of a respective one of the cartridges 26 to rotatably fix the barrel 20 to the indexer 38. As such, rotational movement of the indexer 38 about the drive shaft 24 is translated through the fins 118 to the barrel 20 such that rotational movement of the indexer 38 about the drive shaft 24 effects rotational movement of the barrel 20 about the drive shaft 24.

The cam slot 116 (FIG. 14) of the indexer 38 is positioned to receive a shaft pin 120 formed on a proximal portion of the drive shaft 24 as the indexer 38 nears its retracted or proximal-most position within the housing 12. The shaft pin 120 is positioned to be received within and engage a wall 122 defining the cam slot 116 when the indexer 38 is coupled to the pusher 36 and the pusher 36 and indexer 38 are moved to their proximal-most position to rotate the barrel 120 within the housing 12 as described in detail below.

Referring to FIGS. 18-22, in the open, pre-fired position of the surgical stapling device 10, the anvil 14 is in the open position in relation to the cartridge 26 that is aligned with the anvil 14, i.e., the active cartridge, the pusher 36 is in its proximal-most position located within the first clevis 16, and the annular rib 112 of the indexer 38 is positioned distally of the protrusions 104a of the flexible arms 104 of the pusher 36. In the proximal-most position of the pusher 36, the wings 102 of the pusher 36 are received in the slots 17 (FIG. 3) of the first clevis 16 proximally of the knife slots 74 of the cartridges 26, the beam 108 of the clamping member 101 is positioned proximally of the cam surface 14*a* formed on the proximal end of the anvil 14 (FIG. 20), and the pusher fingers 103 are positioned proximally of the slots 88 defined in each of the cartridge bodies 70.

Referring to FIGS. 23 and 24, as discussed above, the threaded drive shaft 24 is engaged with the threaded bore 40 of the pusher 36. When the drive mechanism 21 (FIG. 6) is actuated to rotate the drive shaft 24, the pusher 36 is driven by the drive shaft 24 distally from within the first clevis 16 into the barrel 20. As the pusher 36 moves distally into the barrel 20, the beam 108 of the pusher 36 moves in the direction indicated by arrow "A" into engagement with the cam surface 14*a* of the anvil 14 to pivot the anvil 14 in the direction indicated by arrow "B" (FIG. 24) from the open position to the clamped position. As the pusher 36 moves distally within the barrel 20, the wings 102 and vertical strut 106 (FIG. 21) of the pusher 36 move through the knife slots 74 of the cartridge 26 and the slots 110 (FIG. 18) of the housing 12 to cofine the pusher 36 to linear movement within the housing 12. The pusher fingers 103 of the pusher 36 also move into the slots 88 of the active cartridge 26 that is aligned with the rows of staples 90.

Figure 27:
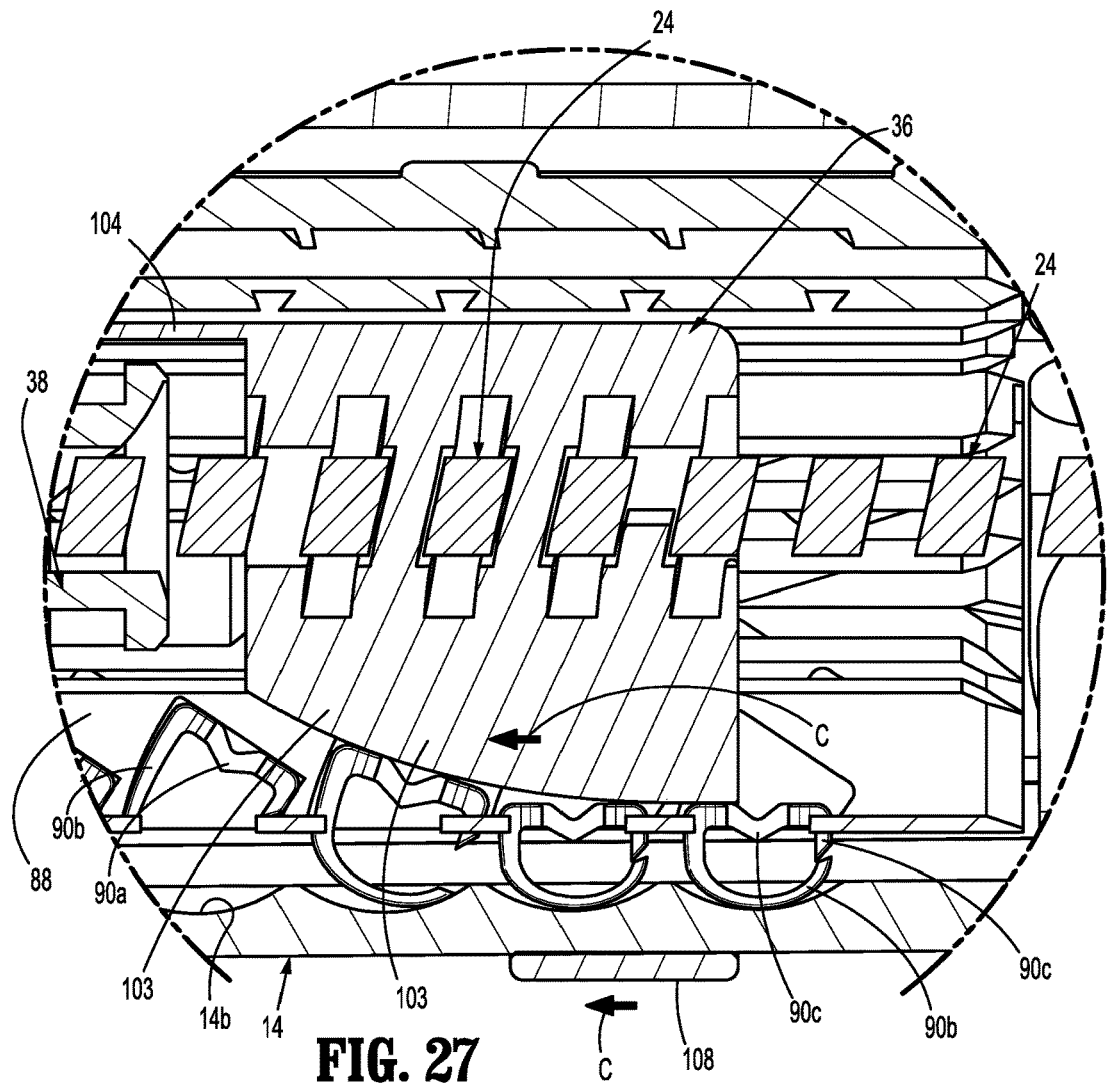
FIG. 27 is an enlarged view of the indicated area of detail shown in FIG. 26.
Figure 28:
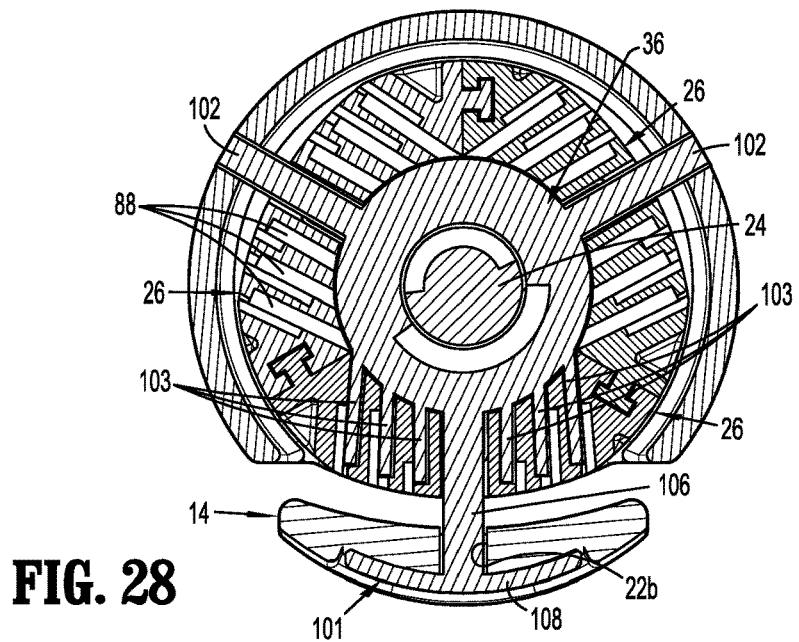
FIG. 28 is a cross-sectional view taken along section line 28-28 of FIG. 26.
Figure 29:
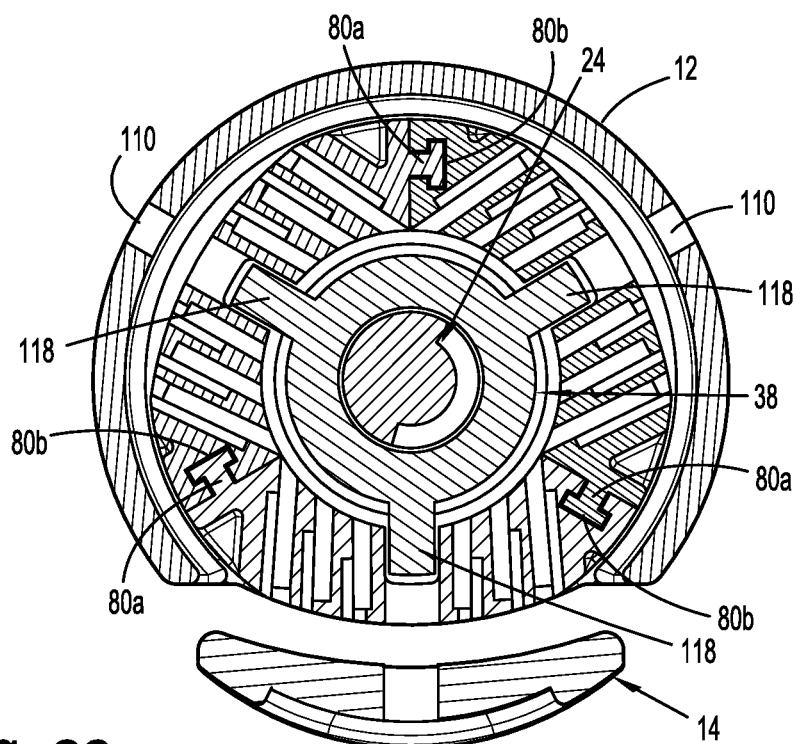
FIG. 29 is a cross-sectional view taken along section line 29-29 of FIG. 26.

Referring to FIGS. 25-30, as the pusher 36 is driven distally in the direction indicated by arrow "C" through the barrel 20 by rotation of the drive shaft 24, the pusher fingers 103 of the pusher 36 translate through the cartridge slots 88 and sequentially engage the staples 90 in the active cartridge 26 to eject the staples 90 into anvil pockets 14*b* of the anvil 14. As discussed above, the pusher fingers 103 engage an offset portion of the backspan 90*a* of each of the staples 90 to drive the first leg 90*b* of each staple 90 into a respective anvil pocket 14*b* to deform the staple 90 into a substantially D-shape (FIG. 27). As illustrated, the vertical strut 106 (FIG. 28) of the clamp member 101 of the pusher 36 travels through the knife slot 22*b* of the anvil 14 such that the beam 108 moves along an outer surface of the anvil 14 in the direction indicated by arrow "C" to maintain a maximum tissue gap in the area where tissue is being stapled. As discussed above, the vertical strut 106 supports a knife 110 that moves between the cartridge 26 and the anvil 14 to transect tissue positioned between the cartridge 26 and the anvil 14.

Figure 30:
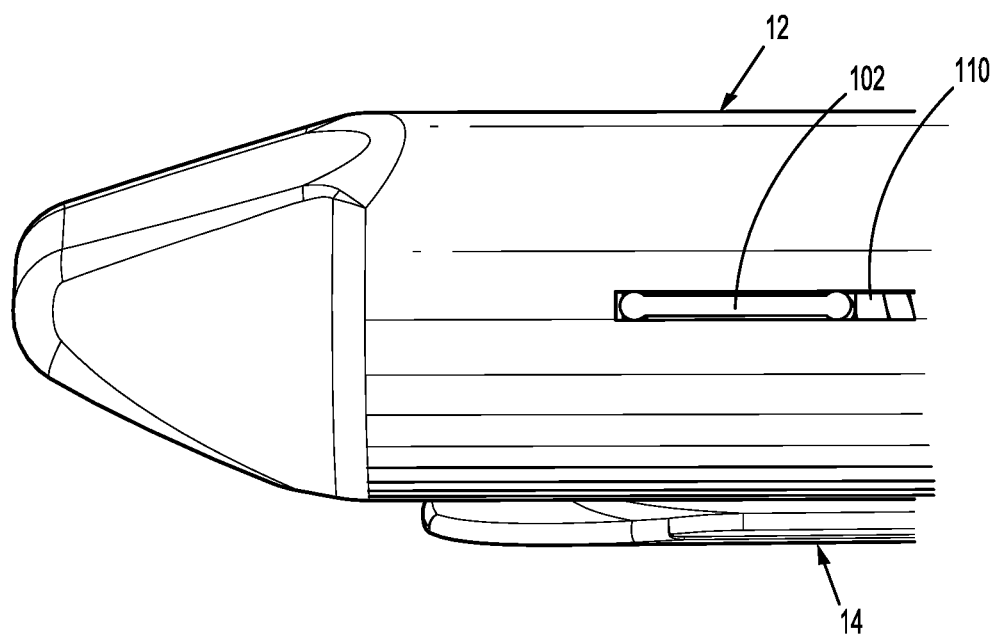
FIG. 30 is a side view of the distal end of the surgical stapling device shown in FIG. 1 after the pusher has been moved to the fully advanced position and the staples from one of the plurality of cartridges have been fired.
Figure 31:
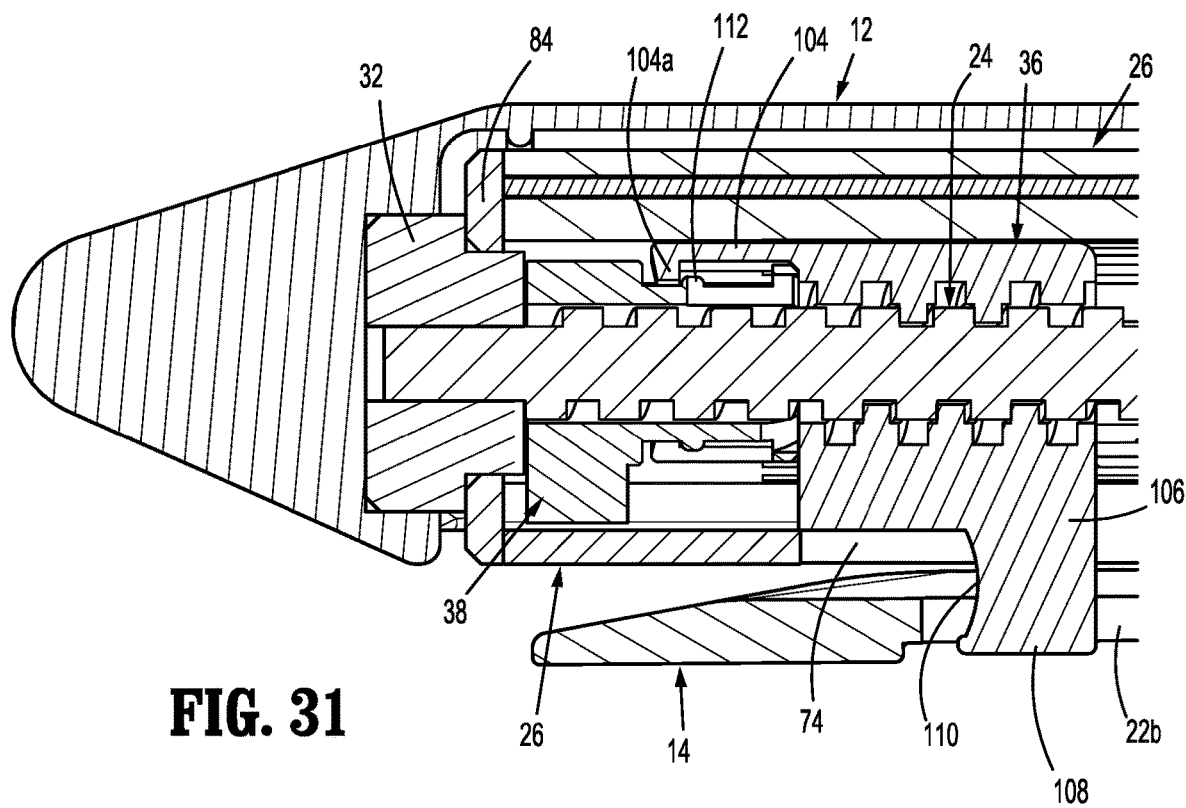
FIG. 31 is a side cross-sectional view of the distal end of the surgical stapling device shown in FIG. 30 after the pusher has been moved to the fully advanced position and the staples from one of the plurality of cartridges have been fired.
Figure 32:
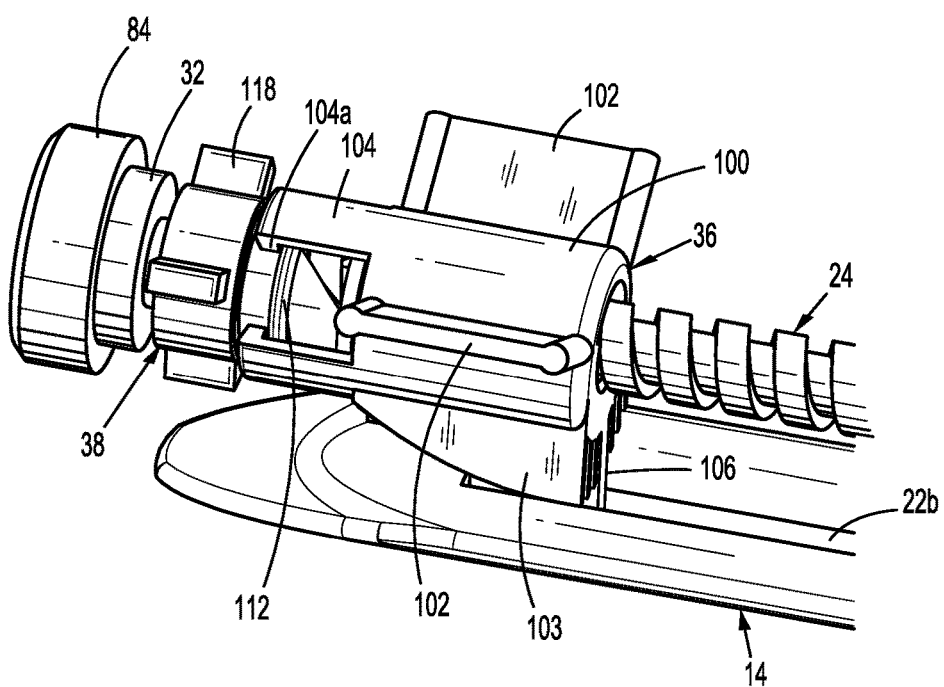
FIG. 32 is a perspective view of the drive shaft, pusher, indexer and anvil assembly in the position as shown in FIG. 31.

Referring to FIGS. 30-32, when the indexer 38 is advanced to its distal-most position in which the indexer 38 abuts the bearing 32, distal movement of the pusher 36 continues independently of the indexer 38 until the flexible arms 104 of the pusher 36 pass over the annular rib 112 on the indexer 38 to position the protrusions 104*a* of the flexible arms 104 at a location distally of the annular rib 112 to releasably couple the pusher 36 with the indexer 38. In this position, the wings 102 of the pusher 36 reach the distal end of the slots 110 of the housing 12 (FIG. 30) to define the distal-most position of the pusher 36.

Figure 33:
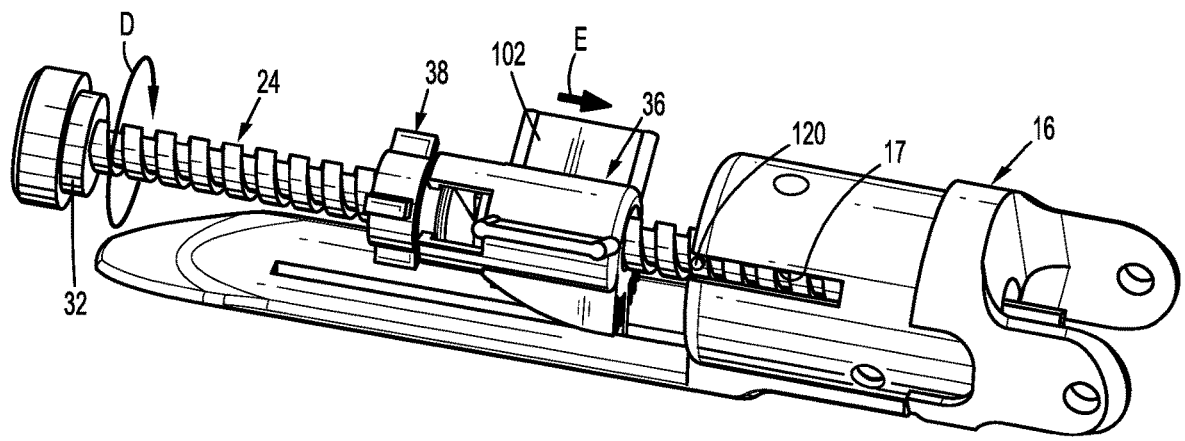
FIG. 33 is a perspective view of the surgical stapling device shown in FIG. 26 with the housing and barrel removed and the pusher and indexer being moved towards the retracted position.
Figure 34:
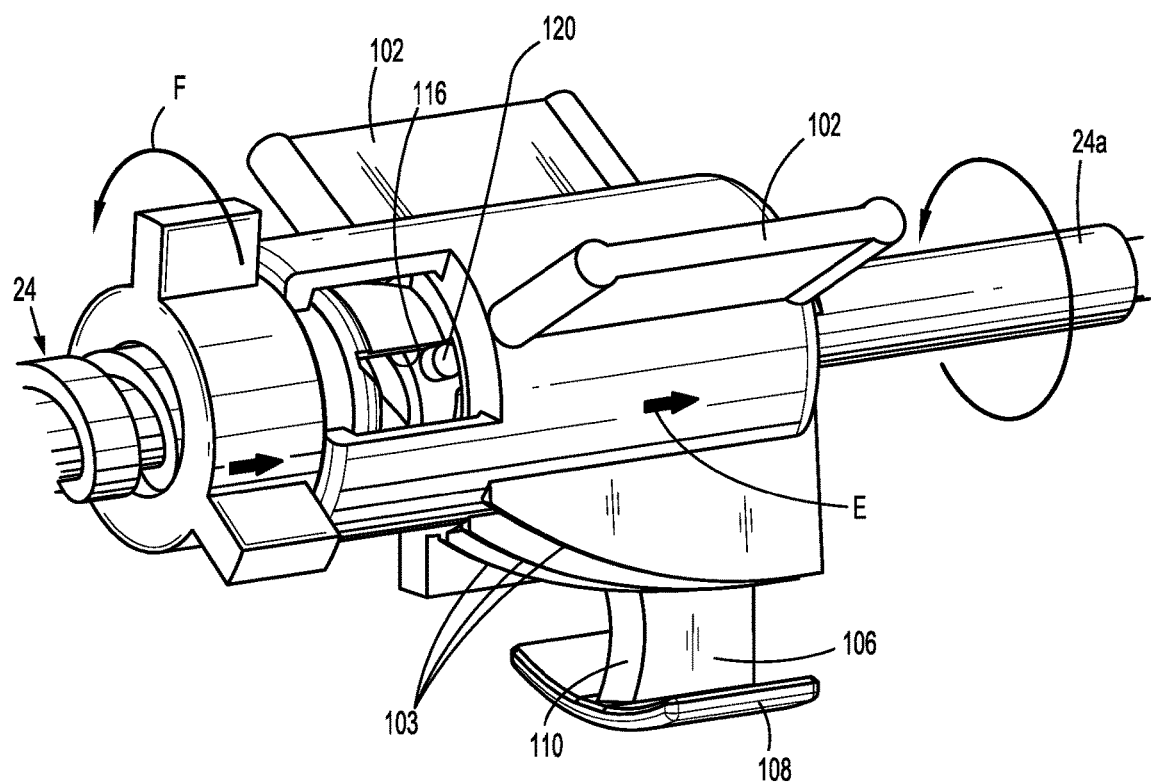
FIG. 34 is a side perspective view of the drive shaft, pusher and indexer as the indexer is rotating the barrel.
Figure 35:
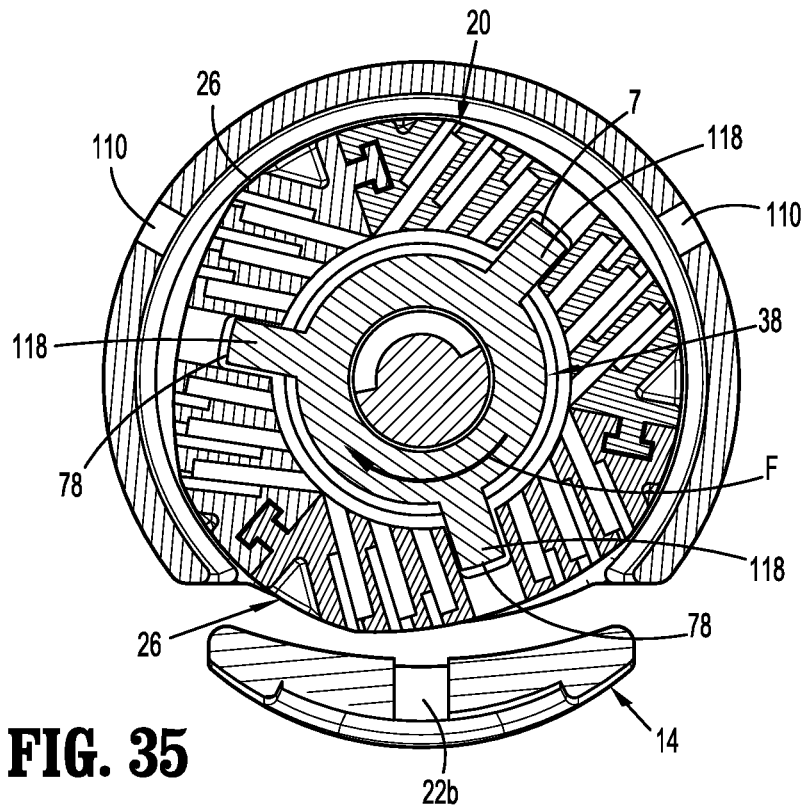
FIG. 35 is a cross-sectional view taken through the surgical stapling device and the indexer as the indexer rotates the barrel.
Figure 36:
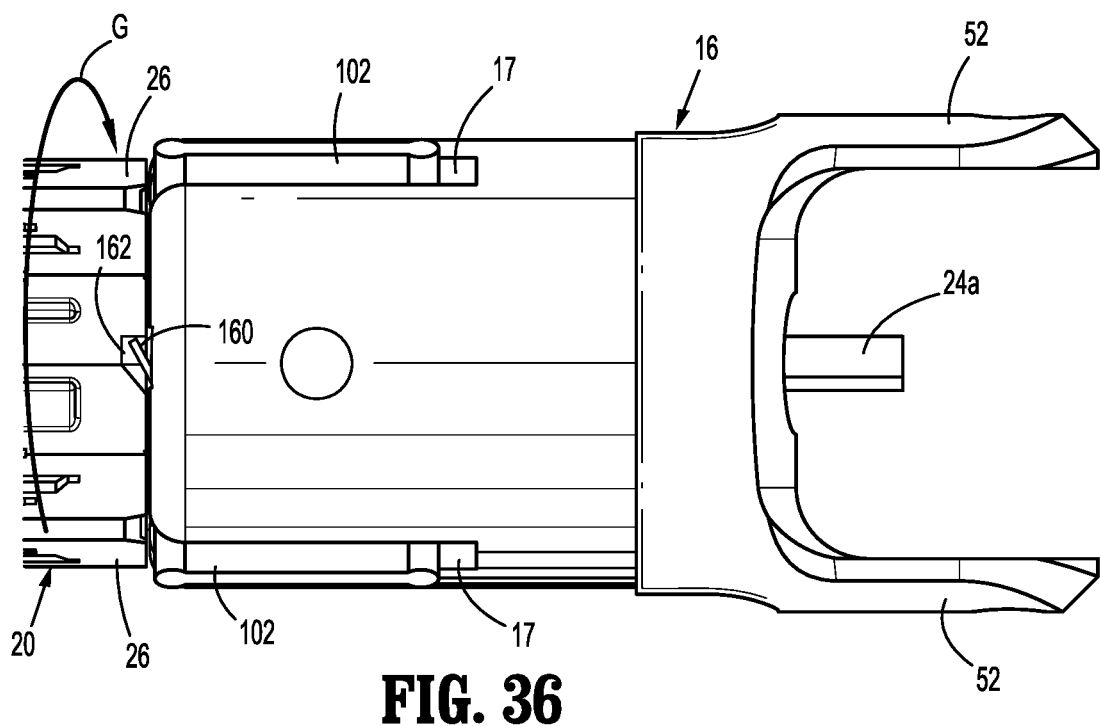
FIG. 36 is a top view of the proximal end of the surgical stapling device shown in FIG. 1 with the housing removed illustrating the locking ratchet.
Figure 37:
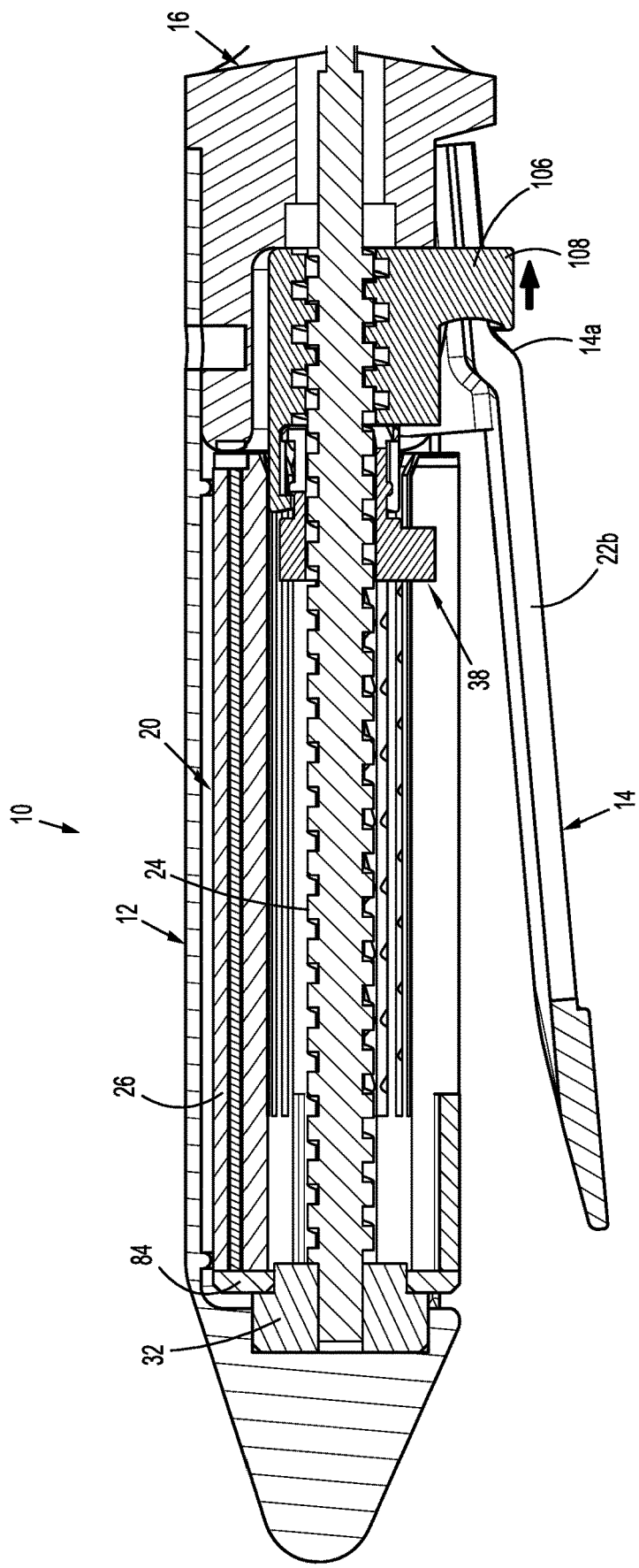
FIG. 37 is a side cross-sectional view of the surgical stapling device shown in FIG. 25 after the device has been fired and the pusher has been moved to its proximal-most position.

Referring to FIGS. 33-37, when the direction of rotation of the drive screw 24 is reversed to rotate in a direction indicated by arrow "D" in FIG. 33, the pusher 36 is retracted within the barrel 20, in the direction indicated by arrow "E" in FIGS. 33 and 34 to cause proximal movement of the indexer 38. As the pusher 36 moves towards its proximal-most position, the wings 102 and vertical strut 106 of the pusher 36 exit the knife slots 74 of the cartridges 26 and pass back into the slots 17 (FIG. 33) of the first clevis 16. Removal of the wings 102 and vertical strut 106 of the pusher 36 from the knife slots 74 frees the barrel 20 for rotation within the housing 12. As the pusher 36 and the indexer 38 are retracted within the housing 12, the shaft pin 120 on the drive shaft 24 engages the inner profile of the cam slot 116 in the indexer 38 (FIG. 34) to effect rotation of the indexer 38 in the direction indicated by arrow "F" in FIG. 34. As noted above, the fins 118 (FIG. 35) of the indexer 38 are positioned within the longitudinal channels 78 of the cartridges 26 such that rotation of the indexer 38 in the direction indicated by arrow "F" in FIG. 35 causes rotation of the barrel 20 within the housing 12 in the direction indicated by arrow "G" in FIG. 36 to reposition a fresh, i.e., unfired, cartridge 26 in opposition to the anvil 14. As shown in FIG. 36, the distal end of the first clevis 16 supports a ratchet 160 that is received within a notch 162 formed at the proximal end of each cartridge 26 to limit rotation of the barrel 20 to rotation in the direction indicated by arrow "G" to prevent the barrel 20 from rotating back to its original position. Movement of the pusher 36 to its proximal-most position moves the beam 108 to a position proximally of the cam surface 14*a* on the anvil 14 to allow the anvil 14 to move back to the open position (FIG. 37).

Figure 38:
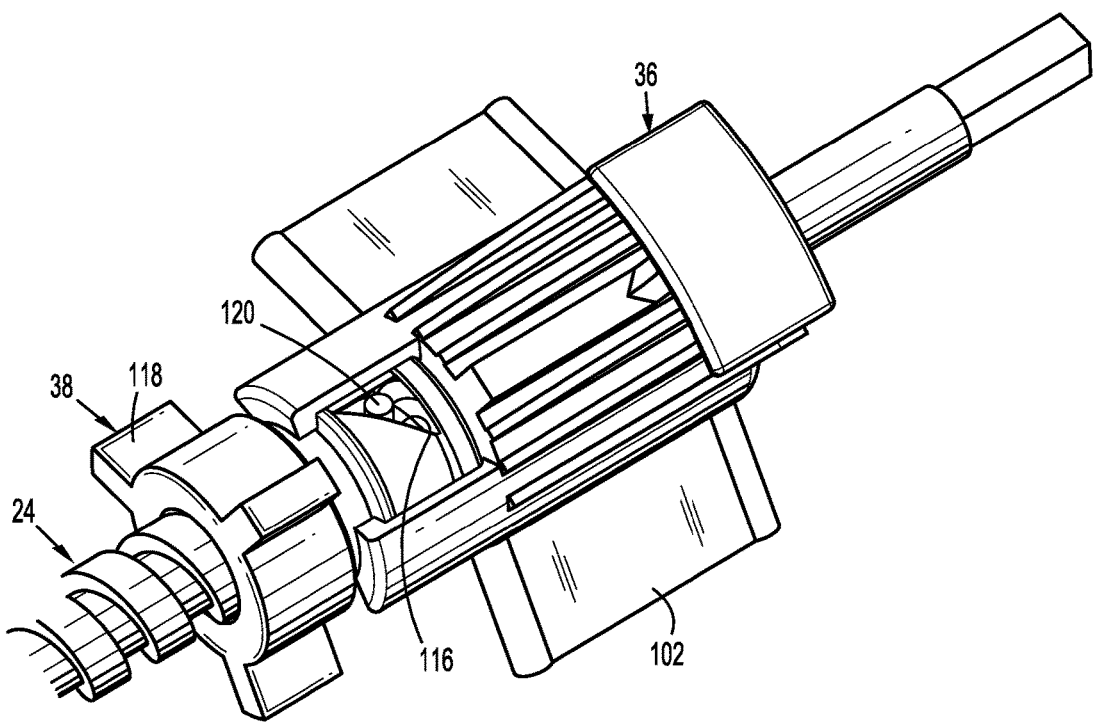
FIG. 38 is a side perspective view of the drive shaft, pusher and indexer after the indexer has rotated the barrel.
Figure 39:
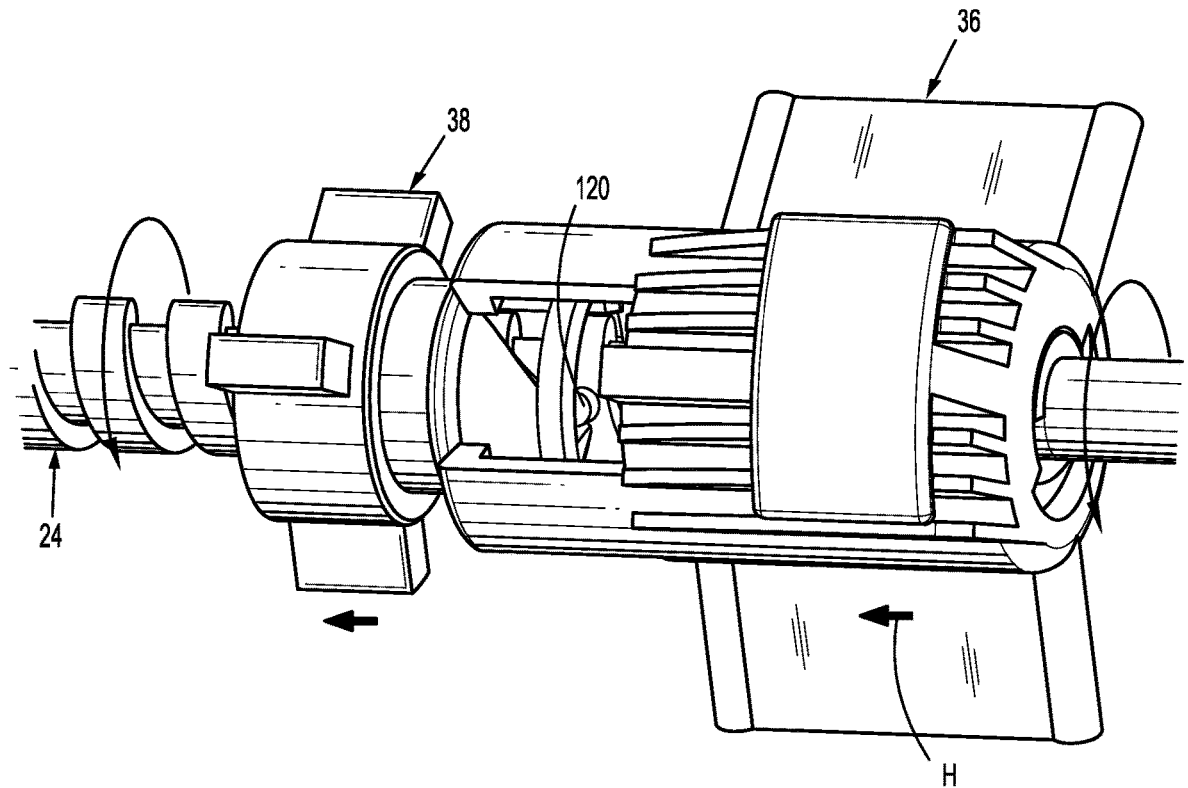
FIG. 39 is a side perspective view of the drive shaft, pusher and indexer after the indexer has rotated the barrel and the pusher is being moved from its proximal-most position to uncouple the indexer from the pusher.

Referring to FIGS. 38 and 39, when the drive shaft 24 is actuated again to advance the pusher 36 distally in the direction indicated by arrow "H", the shaft pin 120 engages the angled profile of the cam slot 116 of the indexer 38 in a direction to advance the indexer 38 distally and to rotate the indexer 38 and, thus, the barrel 20, in a direction opposite to direction "G" (FIG. 36). Since rotation of the barrel 20 in a direction opposite to direction "G" is prevented by the ratchet 160, the indexer 38 is pushed distally by the shaft pin 120 to move the indexer 38 distally in relation to the pusher 36. This relative movement between the pusher 36 and the indexer 38 causes the flexible arms 104 to flex outwardly as the protrusions 104*a* pass back to a position proximally of the annular rib 112. As the pusher 36 is advanced distally to fire staples 90 from the second cartridge 26, the surgical stapling device 10 will function as described above until all of the plurality of cartridges 26 have been fired.

While several embodiments of the disclosure have been described, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A surgical stapling device comprising:
   a housing;
   a staple cartridge supporting a plurality of staples, each of the plurality of staples including a backspan, a first leg having a first length extending from one end of the backspan, a second leg having a second length extending from the other end of the backspan, the first length being greater than the second length, wherein the first and second legs are positioned within a common plane and the backspan has a central portion offset from the common plane;
   an anvil pivotally coupled to the housing, the anvil being movable in relation to the staple cartridge between an open position and a clamped position;
   a drive shaft extending through the housing and through the staple cartridge, and a pusher operatively connected to the drive shaft, the pusher being configured to translate through the staple cartridge to eject the staples from the staple cartridge; and wherein the staple cartridge includes a plurality of cartridges which are coupled together to form a barrel, the barrel being rotatably supported within the housing, each of the cartridges defining a plurality of staple pockets for receiving the plurality of staples.

2. The surgical stapling device of claim 1, wherein the barrel is positioned within the housing to align a first one of the plurality of cartridges with the anvil to eject the plurality of staples from the first cartridge upon movement of the pusher through a first firing stroke and subsequently rotatable within the housing to align a second one of the plurality of cartridges with the anvil to eject the plurality of staples from the second cartridge upon movement of the pusher within the barrel through a second firing stroke.

3. The surgical stapling device of claim 2, wherein the plurality of cartridges includes three cartridges.

4. The surgical stapling device of claim 2, wherein the drive shaft defines a helical thread and the pusher defines a threaded bore, the drive shaft extending through the threaded bore of the pusher such that rotatable movement of the drive shaft causes longitudinal movement of the pusher about the drive shaft and through the barrel.

5. The surgical stapling device of claim 2, further including an indexer supported about the drive shaft at a position distally of the pusher, the indexer being operatively engaged with the barrel and adapted to rotate the barrel after the first firing stroke of the pusher to align the second one of the plurality of cartridges with the anvil.

6. The surgical stapling device of claim 5, wherein the indexer includes a body having a plurality of fins and each of the plurality of cartridges defines a longitudinal channel, each of the longitudinal channels receiving one of the plurality of fins of the indexer to rotatably couple the indexer to the barrel such that rotation of the indexer about the drive shaft causes corresponding rotation of the barrel about the drive shaft.

7. The surgical stapling device of claim 6, wherein a distal end of the pusher is positioned to engage the indexer such that distal movement of the pusher within the barrel causes distal movement of the indexer within the barrel.

8. The surgical stapling device of claim 7, wherein the pusher includes a hub and a plurality of flexible arms that extend distally from the hub, a distal end of each of the flexible arms being positioned to engage the indexer to translate distal movement of the pusher to distal movement of the indexer.

9. The surgical stapling device of claim 8, wherein each of the flexible arms includes an inwardly extending protrusion, the inwardly extending protrusion being configured to engage and pass over an annular rib when the indexer reaches its distal-most position within the housing as the pusher is moved independently of the indexer to its distal-most position to releasably couple the pusher and the indexer such that proximal movement of the pusher through a retraction stroke causes corresponding proximal movement of the indexer.

10. The surgical stapling device of claim 9, further including a ratchet supported adjacent to the barrel, the ratchet being configured to permit rotation of the barrel within the housing in a first direction and prevent rotation of the barrel within the housing in a second direction.

* * * * *